(12) United States Patent
Chan et al.

(10) Patent No.: US 11,850,100 B2
(45) Date of Patent: Dec. 26, 2023

(54) SYSTEMS AND METHODS FOR DETECTING FLOW OF BIOLOGICAL FLUIDS

(71) Applicant: The Children's Mercy Hospital, Kansas City, MO (US)

(72) Inventors: Sherwin S. Chan, Kansas City, MO (US); Justin Baraboo, Kansas City, MO (US)

(73) Assignee: The Children's Mercy Hospital, Kansas City, MO (US)

( * ) Notice: Subject to any disclaimer, the term of this patent is extended or adjusted under 35 U.S.C. 154(b) by 548 days.

(21) Appl. No.: 17/044,610

(22) PCT Filed: Apr. 1, 2019

(86) PCT No.: PCT/US2019/025162
§ 371 (c)(1),
(2) Date: Oct. 1, 2020

(87) PCT Pub. No.: WO2019/195156
PCT Pub. Date: Oct. 10, 2019

(65) Prior Publication Data
US 2021/0196239 A1    Jul. 1, 2021

Related U.S. Application Data

(60) Provisional application No. 62/651,833, filed on Apr. 3, 2018.

(51) Int. Cl.
*A61B 8/08* (2006.01)
*G16H 50/30* (2018.01)
(Continued)

(52) U.S. Cl.
CPC .............. *A61B 8/5223* (2013.01); *A61B 8/06* (2013.01); *A61B 8/461* (2013.01); *A61B 8/488* (2013.01); *G16H 50/20* (2018.01); *G16H 50/30* (2018.01)

(58) Field of Classification Search
CPC ......... A61B 8/5223; A61B 8/06; A61B 8/461; A61B 8/488; A61B 5/0261; A61B 5/0285;
(Continued)

(56) References Cited

U.S. PATENT DOCUMENTS 4,770,184 A * 9/1988 Greene, Jr. ............ G16H 15/00
600/454
4,930,513 A * 6/1990 Mayo ...................... G01P 5/244
600/455

(Continued)

FOREIGN PATENT DOCUMENTS

WO        2019075483         4/2019

OTHER PUBLICATIONS

International Search Report and Written Opinion in corresponding PCT/US2019/025162, dated Jul. 1, 2019.

(Continued)

*Primary Examiner* — Bo Joseph Peng
(74) *Attorney, Agent, or Firm* — Hovey Williams LLP; Crissa Cook

(57) ABSTRACT

A system and computer-implemented method for detecting flow of biological fluid, and facilitating the diagnosis of stenosis or other pathology of a hepatic artery or other non-carotid vasculature by using machine learning to analyze a spectral Doppler ultrasound waveform of blood flow or flow of other biological fluids. A region of interest is identified in a sonogram, a waveform envelope is generated for a waveform within the region of interest, an extracted waveform is generated based on the waveform envelope, a Fourier transform is performed on the extracted waveform, and a Fourier spectrum is generated. Machine learning is used to determine a likelihood of pathology based on waveform parameters, including the Fourier spectrum, and (Continued)

to determine a pathology prediction value. Additional patient information may be accessed and used in determining the likelihood of the pathology.

20 Claims, 11 Drawing Sheets

(51) Int. Cl.
  *G16H 50/20* (2018.01)
  *A61B 8/06* (2006.01)
  *A61B 8/00* (2006.01)
(58) Field of Classification Search
  CPC ... A61B 5/7257; A61B 5/7264; A61B 8/0891; G16H 50/20; G16H 50/30
  See application file for complete search history.

(56) References Cited

U.S. PATENT DOCUMENTS

| | | | | |
|---|---|---|---|---|
| 2013/0137987 | A1* | 5/2013 | Abe | A61B 8/5223 600/454 |
| 2015/0018632 | A1* | 1/2015 | Khair | A61B 5/7225 607/18 |
| 2015/0065864 | A1 | 3/2015 | Sharma et al. | |
| 2016/0157828 | A1* | 6/2016 | Sumi | G01N 29/46 702/189 |
| 2016/0166209 | A1 | 6/2016 | Itu et al. | |
| 2017/0004278 | A1* | 1/2017 | Marsden | G06F 30/23 |
| 2017/0042504 | A1* | 2/2017 | Rich | A61B 8/0883 |

OTHER PUBLICATIONS

Baraboo, et al., "Automated Prediction of Hepatic Arterial Stenosis", AMIA Jt Summits Transl Sci Proc. 2017; 2017:58-65.

Alexandrov, et al., "Correlation of Peak Systolic Velocity and Angiographic Measurement of Carotid Stenosis Revisited", Stroke 1997; 28(2):339-342.

Le, et al., "The Sonographic Stenosis Index: A new specific quantitative measure of transplant hepatic arterial stenosis", J UltrasoundMed 2017:36:809-819.

Dodd, III, et al., "Hepatic artery stenosis and thrombosis in transplant recipients: Doppler diagnosis with resistive index and systolic acceleration time" Radiology 1994;192(3):657-661.

Krishnamoorthy, et al., "Temporal and Spectral Analysis of Internal Carotid Artery Doppler Signal for Normal and Abnormal Flow Detection" IEEE 2015.

Petersen, et al., "The pulsatility index and the resistive index in renal arteries. Associations with long-term progression in chronic renal failure", Nephrol Dial Transplant 1997; 12(7):1376-1380.

Extended Search Report in corresponding European Patent Application Serial No. 19781543.4, dated Nov. 17, 2021.

Wojciechowski, et al., "Non-contact ID vibration analysis in temporal digital speckle photography", Optics and Lasers in Engineering, 2010, 48, pp. 320-324.

\* cited by examiner

SYSTEMS AND METHODS FOR DETECTING FLOW OF BIOLOGICAL FLUIDS

CROSS-REFERENCE TO RELATED APPLICATIONS

The present application is the U.S. National Stage of International Patent Application No. PCT/US2019/025162, filed Apr. 1, 2019, which claims the priority benefit of U.S. Provisional Patent Application Ser. No. 62/651,833, filed Apr. 3, 2018, entitled "SYSTEMS AND METHODS FOR DETECTING FLOW OF BIOLOGICAL FLUIDS," each of which is incorporated by reference in its entirety herein.

FIELD

The present invention relates to systems and methods for detecting and evaluating flow of biological fluids in the body, and in particular, facilitating medical diagnoses of pathologies related thereto. Embodiments concern a system and computer-implemented method for facilitating the medical diagnosis of stenosis or other pathology of a hepatic artery or other non-carotid vasculature by analyzing, in some embodiments analyzing with machine learning, a spectral Doppler ultrasound data, image, and/or waveform of blood flow.

BACKGROUND

Several thousand life-saving liver transplants are performed each year. One of the most common causes of early transplant failure is arterial stenosis of the anastomotic junction between donor and recipient. Early detection of transplant arterial stenosis can help prevent transplant failure and the need to re-transplant. Conventional angiography is the definitive test, but it is expensive and invasive (requiring that an artery be punctured) and the imaging contrast agent can be nephrotoxic and/or trigger immune reactions. An accurate screening test could reduce the number of patients who have to undergo this invasive diagnostic procedure.

Ultrasound imaging of blood flow based on the Doppler effect is the most common screening method, but it suffers from poor specificity. As shown in FIG. 1 PRIOR ART, in a sonogram image 20 illustrating a blood flow velocity waveform, different features based on peak systolic blood flow velocity ("P") 22, end diastolic blood flow velocity ("S") 24, and time ("t") 26 to attain peak velocity have been previously used to predict the presence of stenosis. The classical features 28, illustrated in FIG. 1, for detecting stenosis include a Peak Systolic Velocity, a Resistivity Index ("RI"), a Pulsatility Index, and an Acceleration Time. However, these features and/or values may be of limited accuracy as they suffer from both false positives and false negatives, and may fail to detect narrowing that can progress to stenosis. One reason for their limited predictive accuracy is the fact that they are based on lossy representations that sample blood flow only at a few time points during each cycle. They also highly correlate with each other as features pertaining to peak, trough, or time, which reduces the power of creating models with this set of features.

Currently, a sonographer selects two different points of the waveform in the sonogram image to generate the aforementioned features. This initial step can result in different estimations of the location in the time direction (x axis) and in the velocity direction (y axis) due to human variation alone. These differences can change the classification of stenosis and result in misdiagnoses. Further, the use of the classical features in diagnosing other arteries and vasculature provide dubious results.

Attempts have been made to automate analysis of blood flow downstream of the transplant anastomosis and to compute a Stenosis Index ("SI") for indicating stenosis. SI uses the frequency components of a sonogram waveform, and particularly the ratio of the higher frequency components to the lower fundamental frequency, to determine the likelihood of stenosis. The SI measure, which takes into consideration the entire temporal profile of blood flow, can be thresholded to predict stenosis with 69% sensitivity and 90% specificity. By comparison, the RI has a specificity of 33% in the same patient population. However, the SI measure is currently calculated using interactive software scripts that require intermediate decisions by a human expert, which introduces potential human error. In particular, in order to extract the waveform to calculate the SI, the user must manually refine the region, help guide noise elimination, and trace the waveform. This process is tedious and can be time consuming, and just as sonographers have difficulty consistently identifying peaks and troughs, they also have difficulty consistently calculating SI.

Machine learning approaches have been described for determining the presence of stenosis in the carotid artery through the analysis of sonogram images. However, the carotid artery produces generally ideal waveforms which are generally free from noise and malformations. This is because the carotid artery is very superficial (just under the skin) which requires the ultrasound to traverse less tissue, which reduces reverberation and reflection that leads to noise, and its location in the neck limits the impact of breathing, which eliminates gaps in the waveform. Further, the ease of finding the carotid artery allows for easy resampling if any noise or malformations occur. Thus, machine learning solutions involving the carotid artery are not readily adaptable for use with other vasculature which does not enjoy these advantages. For example, locating a deeper artery can be much more challenging, respiration can cause the artery to move in and out of the imaging field, the orientation of flows can be both toward and away from the probe, and flow in adjacent blood vessels can be superimposed on arterial flow measurements. Additionally, extracting the waveform envelope from the sonogram can be much more difficult due to aliasing of the waveform, "salt and pepper" noise, faint or sparse signals, patchy waveforms with interior "holes," inversion of the waveform, incomplete/interrupted waveform, and wrap around start and end points.

This background discussion is intended to provide information related to the present invention which is not necessarily prior art.

SUMMARY

Embodiments address the above-described and other limitations in the prior art by providing a system and computer-implemented method for facilitating the medical diagnosis of stenosis or other pathology of a hepatic artery or other non-carotid vasculature by analyzing, in some embodiments using machine learning, spectral Doppler ultrasound data representative of blood flow. Such spectral Doppler ultrasound data may be in the form of spectral Doppler ultrasound raw data, as well as a spectral Doppler ultrasound image and/or waveform. Embodiments advantageously provide a non-invasive screening method having higher predictive accuracy and facilitating faster diagnosis than prior art solutions. In particular, employing machine learning advantageously allows for considering a multitude of additional factors and information related to the waveform and/or pathology of interest, whereas prior art solutions only consider one factor.

In one or more embodiments, a system is provided for facilitating a diagnosis of a pathology of a non-carotid vasculature. The system may broadly comprise an ultrasound machine, a processor, and an electronic display. The ultrasound machine may be configured to generate spectral Doppler sonogram data for the non-carotid vasculature. The processor may be configured to perform a machine learning process including generating a plurality of decision trees, evaluating the spectral Doppler sonogram data using the plurality of decision trees, and generating a pathology prediction value. The electronic display may be configured to display a likelihood of pathology based on the pathology prediction value.

In one or more embodiments, a system is provided for facilitating a diagnosis of a pathology of a non-carotid vasculature of a subject. The system may broadly comprise an ultrasound machine, a processor, and an electronic display. The ultrasound machine may be configured to generate spectral Doppler sonogram data for the non-carotid vasculature of the subject. The processor may be configured to receive the sonogram data, and extract a set of quantitative waveform parameters from the sonogram data. The processor may be further configured to determine using a machine learning component a pathology prediction value from the set of quantitative waveform parameters, determine using the machine learning component a determined likelihood of the pathology based on the pathology prediction value (wherein, in one implementation, the determined likelihood may be the pathology prediction value), and estimate an associated error value for the determined likelihood of the pathology. The electronic display may be configured to display the determined likelihood of the pathology and the associated error value for consideration by a healthcare practitioner in the diagnosis of the pathology of the non-carotid vasculature of the subject.

In one or more embodiments, a computer-implemented method is provided for facilitating a diagnosis of a pathology of a non-carotid vasculature. The computer-implemented method may broadly comprise the following. Spectral Doppler sonogram data for the non-carotid vasculature may be generated using an ultrasound machine. A plurality of decision trees may be generated, the spectral Doppler sonogram data may be evaluated using the plurality of decision trees, and a pathology prediction value may be generated by processor using a machine learning process. A pathology prediction based on the pathology prediction value may be displayed on an electronic display.

In one or more embodiments, a computer-implemented method is provided for improving the function of a computer for facilitating a diagnosis of a pathology of a non-carotid vasculature of a subject. The computer may include a processor. The computer-implemented method may broadly comprise the following. Spectral Doppler sonogram data for the non-carotid vasculature of the subject may be generated using an ultrasound machine and received by the processor. The processor may extract a set of quantitative waveform parameters from the sonogram data. The processor may further determine using a machine learning component a pathology prediction value from the set of quantitative waveform parameters, determine using the machine learning component a determined likelihood of the pathology based on the pathology prediction value (wherein, in one implementation, the determined likelihood may be the pathology prediction value). The determined likelihood of the pathology may be displayed on an electronic display for consideration by a healthcare practitioner in the diagnosis of the pathology of the non-carotid vasculature of the subject.

Various implementations of these embodiments may include any one or more of the following features. The non-carotid vasculature may be a hepatic artery, and the pathology may be stenosis. The processor may be incorporated into the ultrasound machine, or the computer may be distinct from the ultrasound machine. The machine learning component may use a random forest model comprising a plurality of decision trees. The spectral Doppler sonogram data may comprise a spectral Doppler sonogram image. Extracting the set of quantitative waveform parameters from the spectral Doppler sonogram data may include finding a region of interest in the spectral Doppler sonogram image, extracting a waveform from the region of interest to produce an extracted waveform, and performing a Fourier transform of the extracted waveform and generating a Fourier spectrum, wherein the Fourier spectrum is the set of quantitative waveform parameters. The waveform may be extracted using an edge detection filter. The processor may be further configured to, between extracting the waveform envelope and performing the Fourier transform, compensate for signal noise in the extracted waveform, isolate a corrupted section of the extracted waveform, and determine an optimal sonogram waveform subsequence. The processor may be further configured to access additional information about the subject which is relevant to the pathology, in which case determining the likelihood of the pathology may be based on the pathology prediction value and the additional information. The processor may be further configured to estimate an associated error value for the determined likelihood of the pathology. The associated error value may be displayed on the electronic display for consideration by the healthcare practitioner.

In one or more embodiments, a system is provided for facilitating a diagnosis of a pathology of a non-carotid vasculature. The system may broadly comprise an ultrasound machine, a processor, and an electronic display. The ultrasound machine may be configured to generate a spectral Doppler sonogram image of the non-carotid vasculature. The processor may be configured to perform a machine learning process including generating a plurality of decision trees, evaluating the spectral Doppler sonogram image using the plurality of decision trees, and generating a pathology prediction value. The electronic display may be configured to display a likelihood of pathology based on the pathology prediction value.

In one or more embodiments, a system is provided for facilitating a diagnosis of a pathology of a non-carotid vasculature of a subject. The system may broadly comprise an ultrasound machine, a processor, and an electronic display. The ultrasound machine may be configured to generate a spectral Doppler sonogram image of the non-carotid vasculature of the subject. The processor may be configured to receive the sonogram image, and extract a set of quantitative waveform parameters from the sonogram image. The processor may be further configured to determine, using a machine learning component, a pathology prediction value from the set of quantitative waveform parameters; determine, using the machine learning component, a determined likelihood of the pathology based on the pathology prediction value (wherein, in one implementation, the determined likelihood may be the pathology prediction value); and estimate an associated error value for the determined likelihood of the pathology. The electronic display may be configured to display the determined likelihood of the pathology and the associated error value for consideration by a healthcare practitioner in the diagnosis of the pathology of the non-carotid vasculature of the subject.

In one or more embodiments, a computer-implemented method is provided for facilitating a diagnosis of a pathology of a non-carotid vasculature. The computer-implemented method may broadly comprise the following. A spectral Doppler sonogram image of the non-carotid vasculature may be generated using an ultrasound machine. A plurality of decision trees may be generated, the spectral Doppler sonogram image may be evaluated using the plurality of decision trees, and a pathology prediction value may be generated by a processor using a machine learning process. A pathology prediction based on the pathology prediction value may be di splayed on an electronic display.

In one or more embodiments, a computer-implemented method is provided for improving the function of a computer for facilitating a diagnosis of a pathology of a non-carotid vasculature of a subject. The computer may include a processor. The computer-implemented method may broadly comprise the following. A spectral Doppler sonogram image of the non-carotid vasculature of the subject may be generated using an ultrasound machine and received by the processor. The processor may extract a set of quantitative waveform parameters from the sonogram image. The processor may further determine, using a machine learning component, a pathology prediction value from the set of quantitative waveform parameters; and determine, using the machine learning component, a determined likelihood of the pathology based on the pathology prediction value (wherein, in one implementation, the determined likelihood may be the pathology prediction value). The determined likelihood of the pathology may be displayed on an electronic display for consideration by a healthcare practitioner in the diagnosis of the pathology of the non-carotid vasculature of the subject.

Various implementations of these embodiments may include any one or more of the following features. The non-carotid vasculature may be a hepatic artery, and the pathology may be stenosis. The processor may be incorporated into the ultrasound machine, or the computer may be distinct from the ultrasound machine. The machine learning component may use a random forest model comprising a plurality of decision trees. Extracting the set of quantitative waveform parameters from the spectral Doppler sonogram image may include finding a region of interest in the spectral Doppler sonogram image, extracting a waveform from the region of interest to produce an extracted waveform, and performing a Fourier transform of the extracted waveform and generating a Fourier spectrum, wherein the Fourier spectrum is the set of quantitative waveform parameters. The waveform may be extracted using an edge detection filter. The processor may be further configured to, between extracting the waveform envelope and performing the Fourier transform, compensate for signal noise in the extracted waveform, isolate a corrupted section of the extracted waveform, and determine an optimal sonogram waveform subsequence. The processor may be further configured to access additional information about the subject which is relevant to the pathology, in which case determining the likelihood of the pathology may be based on the pathology prediction value and the additional information. The process may be further configured to estimate an associated error value for the determined likelihood of the pathology. The associated error value may be displayed on the electronic display for consideration by the healthcare practitioner.

This summary is not intended to identify essential features of the present invention, and is not intended to be used to limit the scope of the claims. These and other aspects of the present invention are described below in greater detail.

DRAWINGS

Embodiments of the present invention are described in detail below with reference to the attached drawing figures, wherein:

FIG. 1 PRIOR ART is an example sonogram image showing two points of information and equations for deriving features used by prior art techniques;

The figures are not intended to limit the present invention to the specific embodiments they depict. The drawings are not necessarily to scale.

DETAILED DESCRIPTION

The following detailed description of embodiments of the invention references the accompanying figures. The embodiments are intended to describe aspects of the invention in sufficient detail to enable those with ordinary skill in the art to practice the invention. The embodiments of the invention are illustrated by way of example and not by way of limitation. Other embodiments may be utilized and changes may be made without departing from the scope of the claims. The following description is, therefore, not limiting. The scope of the present invention is defined only by the appended claims, along with the full scope of equivalents to which such claims are entitled.

In this description, references to "one embodiment," "an embodiment," or "embodiments" mean that the feature or features referred to are included in at least one embodiment of the invention. Separate references to "one embodiment," "an embodiment," or "embodiments" in this description do not necessarily refer to the same embodiment and are not mutually exclusive unless so stated. Specifically, a feature, component, action, step, etc. described in one embodiment may also be included in other embodiments, but is not necessarily included. Thus, particular implementations of the present invention can include a variety of combinations and/or integrations of the embodiments described herein.

Figure 1:
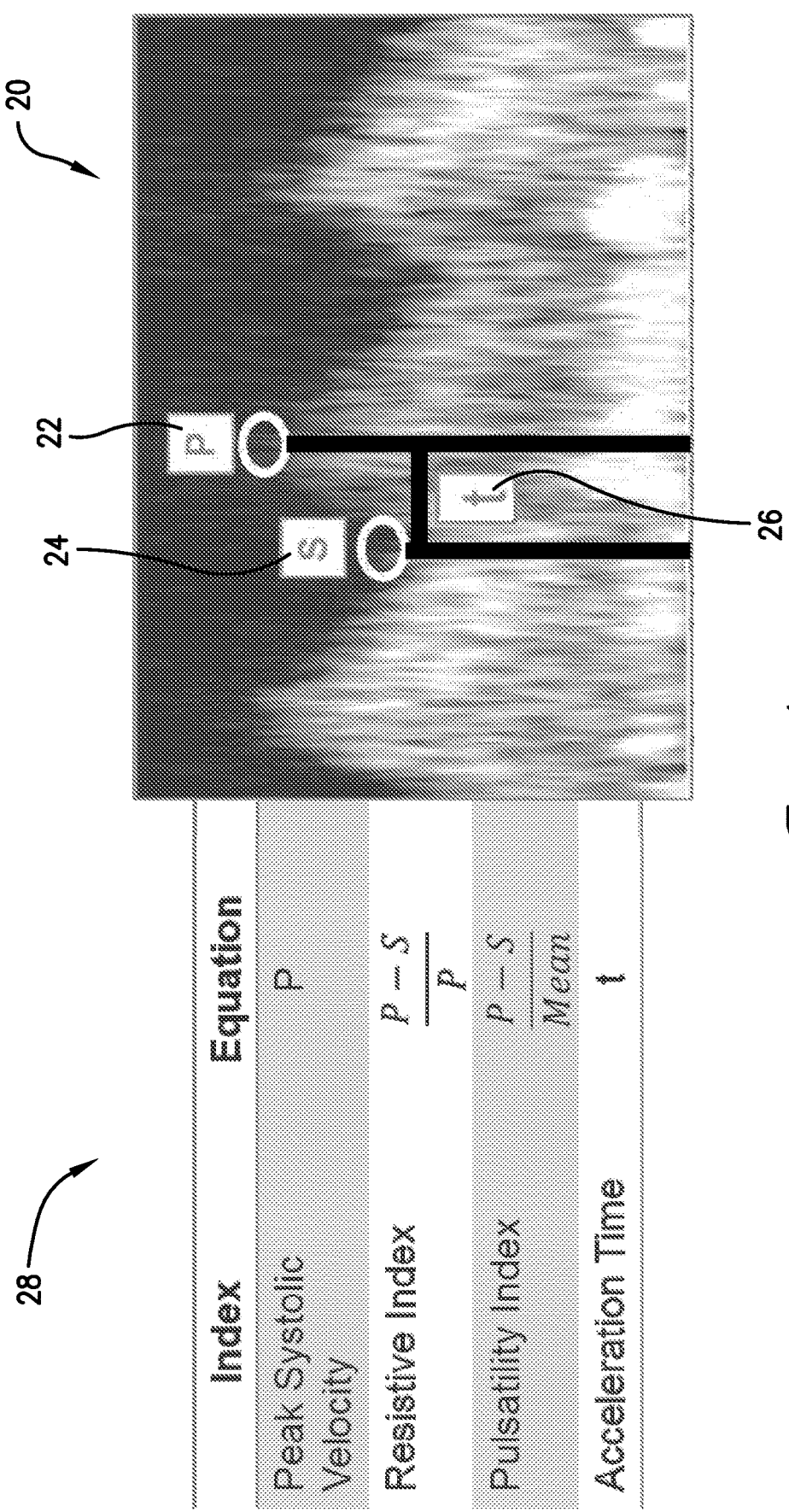

Broadly, embodiments of the present invention concern systems and computer-implemented methods for detecting the flow of biological fluids through a conduit, and facilitating medical diagnosis of stenosis or other pathology of a hepatic artery or other non-carotid vasculature by analyzing, in some embodiments using a machine learning component, spectral Doppler ultrasound data, image, and/or waveform of detected blood flow. In more detail, embodiments of the present invention automate the extraction of a waveform and feature characteristics from noisy, real-world sonograms images of biological fluid flows, apply Fourier analysis for comprehensive analysis of the fluid flows, and use this information in both building machine learning models and classifying vascular pathology. In one implementation, for example, the machine learning component may utilize a decision tree learning model, which uses quantitative waveform parameters extracted from the blood flow velocity waveform for purposes of classifying vascular pathology. The quantitative waveform parameters may include temporal and/or spectral features of the waveform (e.g., a Fourier spectrum), the peak value of the waveform (e.g., "P" from FIG. 1), the trough value of the waveform (e.g., "S" from FIG. 1), the acceleration and/or the time between the peak value and the trough value of the waveform (e.g., "t" from FIG. 1), the mean value of the waveform, the wavelength of the waveform, the frequency of the waveform, or other waveform data that can be measured and/or extracted from the waveform. In some specific embodiments, as will be discussed in more detail below, embodiments may utilize a random forest model of machine learning, which uses a plurality of decision trees to classify vascular pathology and/or to determine a likelihood of the vascular pathology. Some embodiments may use the machine learning component to generate a scoring model for estimating vascular pathology. Embodiments may use other suitable machine learning models/techniques, such as support vector machines, k-nearest neighbors, principal component analysis, and/or neural networks.

When using the machine learning component, some embodiments may additionally incorporate other relevant information about the patient or other subject (referred to herein as "patient information"), e.g., age, sex, drug use, liver or other relevant enzyme levels in the blood, to aid in creating a scoring model for estimating vascular pathology. More specifically, the machine learning component may receive and use the relevant patient information to augment the waveform parameters in the decision-making process when building and implementing the scoring model. This augmentation can be utilized in any machine learning model that uses a scoring mechanism to make determinations. The augmentation may be used by the scoring mechanism of one model to determine the estimate of pathology (referred to herein as "likelihood of pathology" or "pathology prediction"), or may be used by combining multiple models (e.g., one for the waveform parameters and another for the additional patient information) to determine the estimate of pathology.

In one embodiment, an automated clinical decision support tool may be provided for predicting and facilitating the diagnosis of hepatic arterial stenosis in liver transplant recipients, based on a Fourier spectrum analysis of an ultrasound sonogram image waveform to compute an SI, and employing machine learning to increase predictive power. In other implementations, the automated clinical decision support tool may be used for the prediction and/or diagnosis of pathologies of substantially any non-carotid artery or other vasculature, such as visceral, extremity, and/or intercranial vasculature.

Embodiments advantageously provide a non-invasive screening method having higher predictive accuracy and facilitating faster diagnosis than prior art solutions. In particular, employing machine learning advantageously allows for considering a multitude of additional factors and information related to the waveform and/or pathology of interest, whereas prior art solutions only consider one factor.

Although generally described herein in the example context of blood flowing through non-carotid vasculature, it will be understood and appreciated that the present technology may be used in other contexts involving a biological fluid, such as urine or cerebrospinal fluid, which can be detected flowing through a biological conduit within a subject (e.g., artery/vein, ureter/urethra, spinal meninges/nerves, or other tube-shaped vessels that carry fluids within the body). In particular, the systems and methods described herein can be useful in detecting abnormalities in flow of the biological fluid through the biological conduit.

Figure 2:
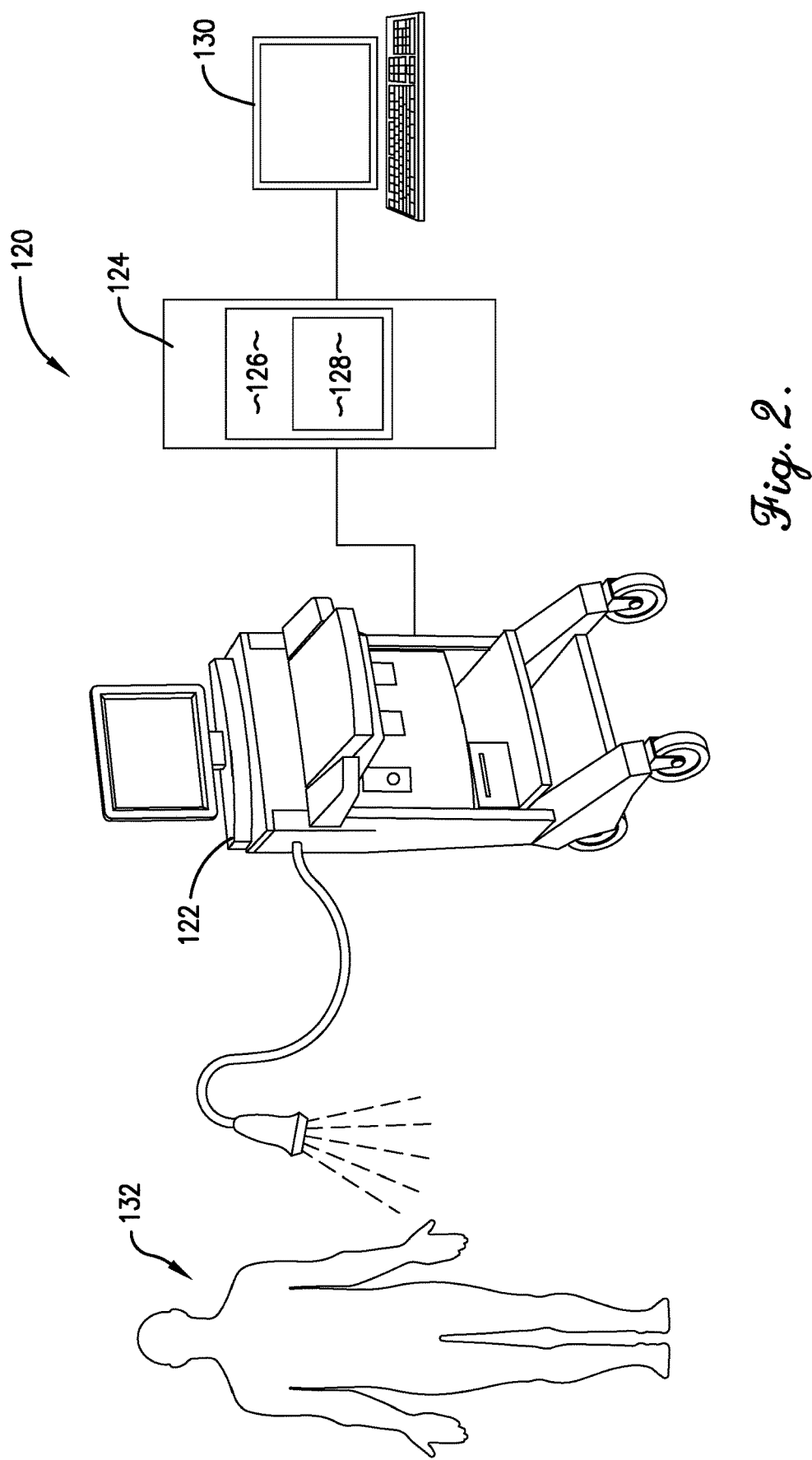
FIG. 2 is a diagram of an embodiment of a system for facilitating the diagnosis of a pathology of a non-carotid vasculature of a subject, according to embodiments of the present invention.
Figure 3:
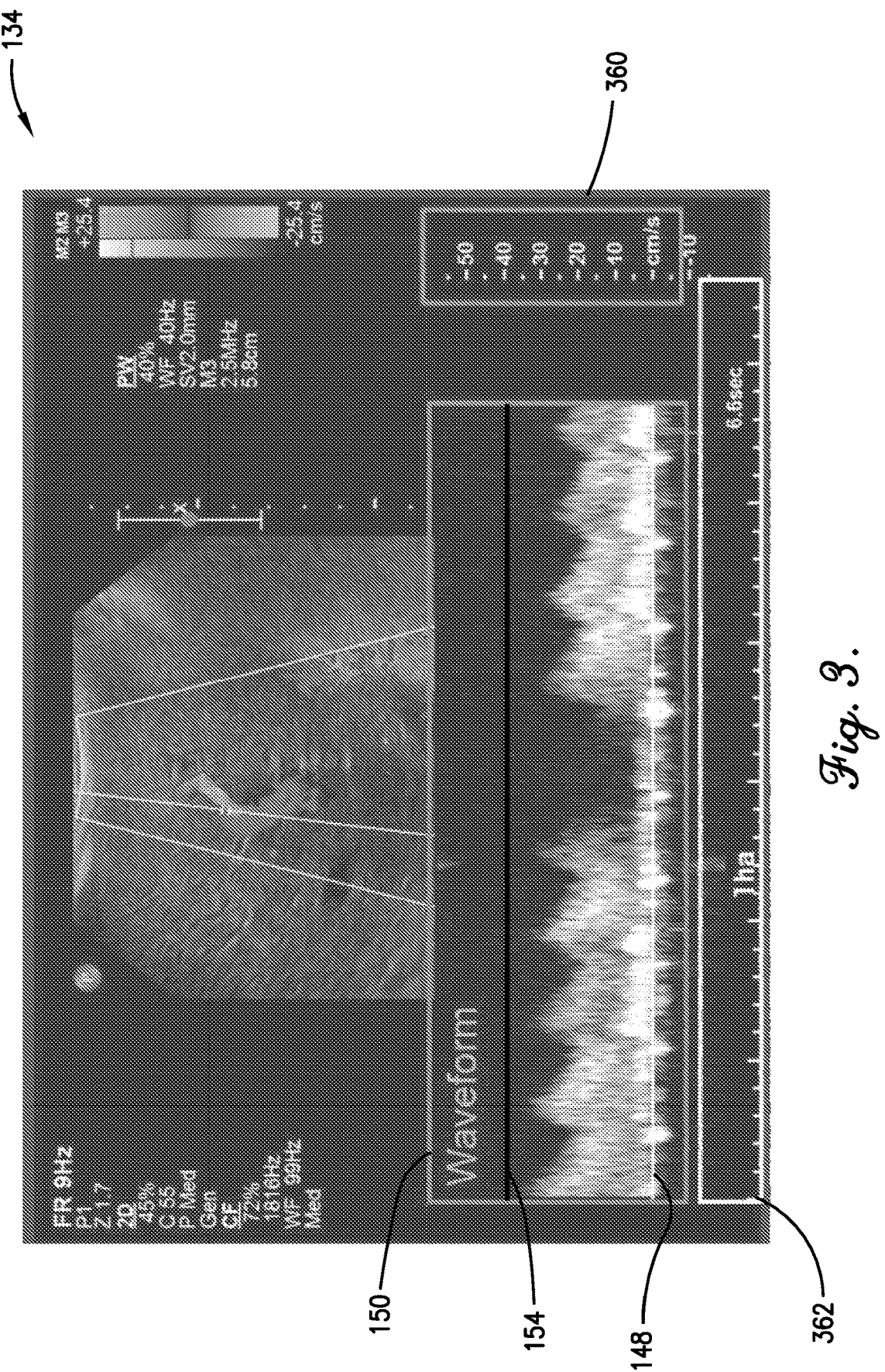
FIG. 3 is an exemplary sonogram image generated by an ultrasound machine component of the system of FIG. 2.

Referring to FIG. 2, an embodiment of a system 120 is shown for facilitating the diagnosis of a pathology of a non-carotid artery or other vasculature by analyzing, in some embodiments using machine learning, a spectral Doppler sonogram image of blood flow in the vasculature. The system 120 may broadly comprise an ultrasound machine 122, a computer 124 including a processing element 126 executing a computer program that may be stored on a memory element 128, and a display device 130. The ultrasound machine 122 may be substantially any otherwise conventional or non-conventional ultrasound machine configured to detect/measure the velocity of blood flow (or other fluid flow) through the vasculature of a subject 132 and to generate sonogram images containing information about the velocity of blood flow (or other fluid flow) through the vasculature of a subject 132. An exemplary sonogram image 134 is shown in FIG. 3.

The computer 124, including the processing element 126, may be substantially any conventional or non-conventional computing device, with one or more processing elements 126 and/or one or more memory elements 128, which is configured to receive information/data from the ultrasound machine 122, execute the computer program stored on the memory element 128, and to provide output to the display device 130. In alternative embodiments, the computer 124 may be part of or distinct from the ultrasound machine 122. As discussed in more detail below, the computer program may be configured to perform the steps, functions, and/or features of embodiments of the present invention described herein. For example, the computer program may be configured to obtain and analyze waveform parameters from waveforms included in sonogram images, and in some embodiments to use machine learning, so as to determine a pathology prediction value and/or to otherwise determine a likelihood of the pathology of the vasculature of the subject 132. Thus, the computer program may be comprised as one or more software programs, instructions, commands, code, code segments, executables, applications, apps, and the like, which is stored on the memory elements 128 for performing certain of the operations described herein. As such, the computer 124 may be a special purpose computer that is programmed to perform the operations, methods, steps, tasks, an/or algorithms, disclosed herein.

The processing elements 126 of the computer 124 may comprise processors, microprocessors, microcontrollers, field programmable gate arrays, and the like, or combinations thereof. In addition, the processing elements 126 may include one or more internal levels of cache (not shown). The memory elements 128 may also be known as a "computer-readable storage medium" and may include random access memory (RAM), read only memory (ROM), flash drive memory, floppy disks, hard disk drives, optical storage media such as compact discs (CDs or CDROMs), digital video disc (DVD), Blu-Ray and the like, or combinations thereof. In addition to these memory elements 128, the system 120 may further include file stores comprising a plurality of hard disk drives, network attached storage, or a separate storage network.

The display device 130 may be substantially any otherwise conventional or non-conventional display device configured to display the output information provided by the processing element 126 of the computer 124. In alternative implementations, the display device 130 may be part of or distinct from the ultrasound machine 122.

Figure 4:
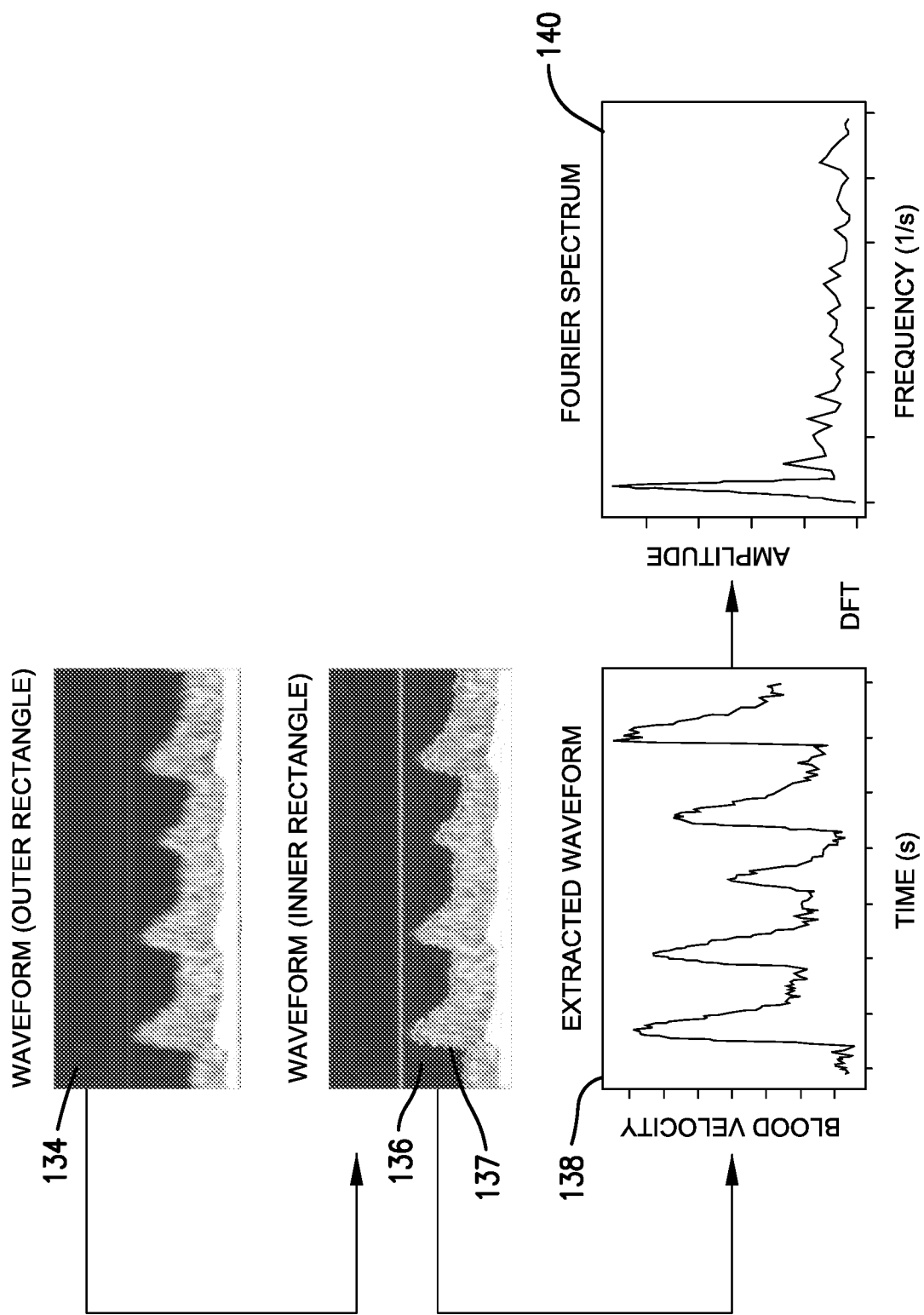
FIG. 4 is a schematic illustration of a method for facilitating the diagnosis of a pathology of a non-carotid artery or other vasculature, according to embodiments of the present invention.

Referring to FIG. 4, the embodiment of the system 120 may function substantially as follows. The ultrasound machine 122 may obtain and/or generate a spectral Doppler sonogram image 134 of a hepatic artery, or other non-carotid vasculature, of a patient. The sonogram image 134 may include a color-based representation of blood flow and velocity through the vasculature (not shown in FIG. 4; see, instead, upper half of sonogram image 134 in FIG. 3). In addition, the sonogram image 134 may include a two-dimensional waveform, as shown in white on FIG. 4, that represents blood flow velocity as a function of time through the subject's 132 vasculature. On the sonogram image 134, an x-axis of the waveform represents time, and the y-axis represents velocity. In more detail, the sonogram image 134 can be defined as a digital image that can be obtained by the ultrasound machine 122 and stored on the memory element 128 of the computer. The sonogram image 134 may further be presented on an electronic display (e.g., the display device 130) as a two-dimensional array of pixels. Thus, the sonogram image 134 will present a waveform that is illustrative of the blood flow velocity through the non-carotid artery of the subject 132. Specifically, the pixels of the sonogram image 134 that represent the waveform may be activated to "solid white," while the pixels of the sonogram image 134 that do not represent the waveform will be deactivated to "solid black."

From the sonogram image 134, embodiments provide for a set of quantitative waveform parameters to be extracted from the waveform. In one embodiment, and with reference to FIG. 4, extracting the set of waveform parameters may comprise the following steps (which may be performed by the computer program of the present embodiments): finding a region of interest 136 within the sonogram image 134, generating a waveform envelope 137 for the waveform within the region of interest 136, producing an extracted waveform 138 based on the waveform envelope 137, performing a discrete Fourier transform on the extracted waveform 138, and generating a Fourier spectrum 140, wherein the Fourier spectrum may, in some embodiments, comprise the set of waveform parameters. In some embodiments, the computer program may be used to analyze the set of quantitative waveform parameters (e.g., the Fourier spectrum 140) to determine a pathology prediction value which can be used as the basis for making a prediction about whether the vascular pathology (e.g., stenosis) is present. The pathology prediction value may include generally any type of value that can be used to provide an estimate of pathology. For example, the pathology prediction value may be a SI value or another value based on the extracted waveform (e.g., a PI value, acceleration time, global frequency, and/or right and left half-lives). The right and left half-lives are the time it takes the blood flow velocity to reduce to half the distance from the peak systolic velocity to the diastolic velocity on the right and left side of the peak systolic velocity. In some additional embodiments, a machine learning component of the computer program may be used to analyze the set of quantitative waveform parameters (e.g., the Fourier spectrum 140) and to generate the pathology prediction value. In some of such embodiments, the machine learning component may use a unique scoring model to generate a pathology prediction value that is indicative of the pathology. As used herein, the term machine learning component may mean software programs, instructions, commands, code, code segments, executables, applications, apps, or portions thereof, that form at least part of the computer program of embodiments of the present invention, and which incorporate at least some machine learning processes, models, techniques, or the like.

Based on the pathology prediction value, embodiments may generate a likelihood of pathology (also referred to as a "pathology prediction"). In some embodiments, the likelihood of pathology may simply be the pathology prediction value. Alternatively, the likelihood of pathology may comprise a classification scheme that can be used to estimate and indicate the probability of pathology. For example, the likelihood of pathology may be in the text-based scheme of: a "high likelihood," a "moderate likelihood," or a "low likelihood" that the patient is experiencing stenosis (or another pathology). Alternatively, or in addition, the likelihood of pathology can include other classifications schemes, such as a color-based scheme (e.g., red (high likelihood), yellow (moderate likelihood), green (low likelihood)), a number-based scheme (e.g., percentages), or the like. Regardless, embodiments provide for the likelihood of pathology to be communicated to a healthcare practitioner who may consider the likelihood of pathology and/or the pathology prediction value when diagnosing the pathology. For example, in some embodiments, the likelihood of pathology and/or the pathology prediction value may be presented via the display device 130.

The system 120 may include more, fewer, or alternative components and/or perform more, fewer, or alternative actions, including those discussed elsewhere herein, and particularly those discussed in the following section describing the computer-implemented method.

Figure 5:
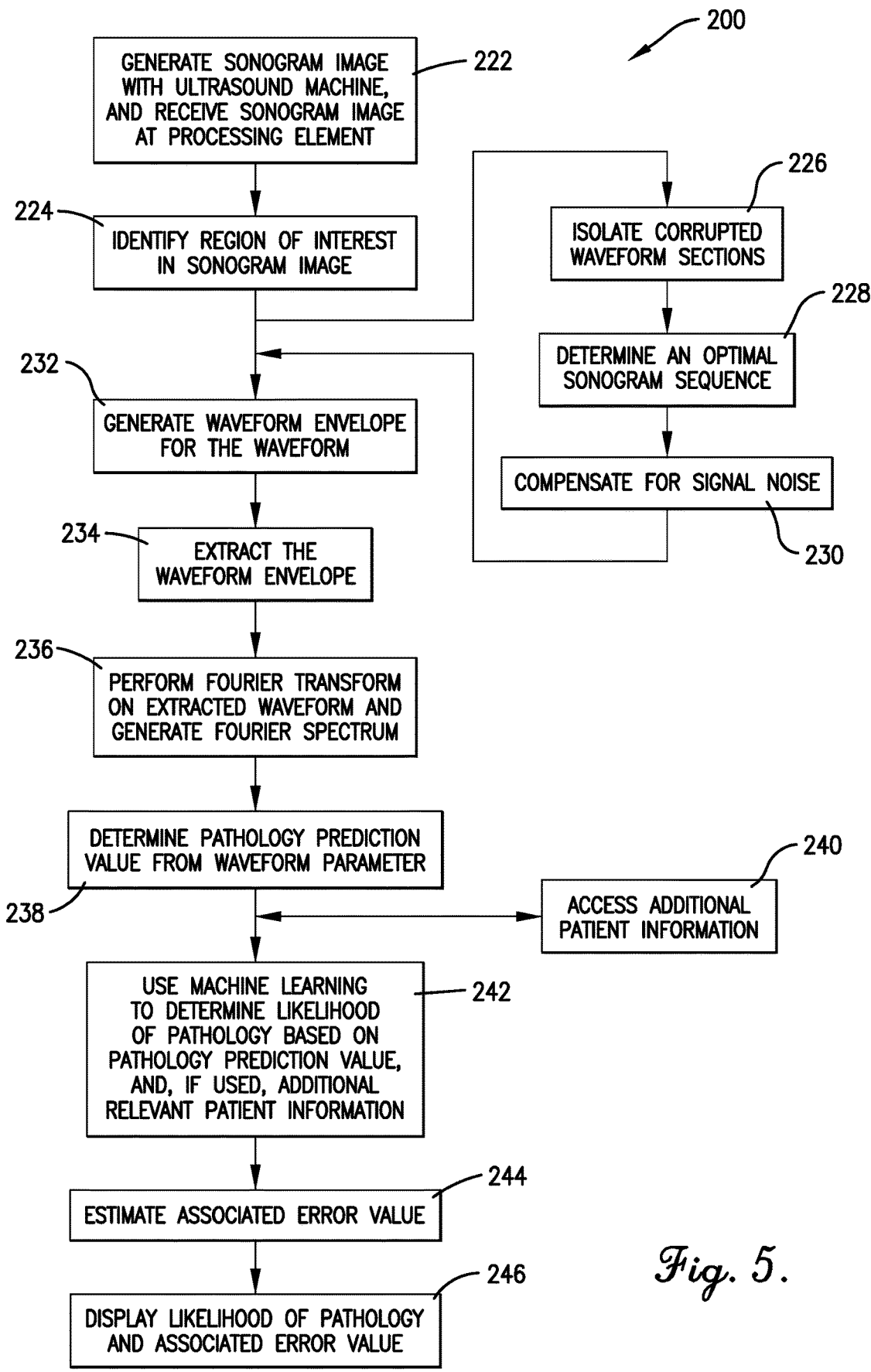
FIG. 5 is a flowchart of steps of a method for facilitating the diagnosis of a pathology of a non-carotid artery or other vasculature, according to embodiments of the present invention.

Referring now to FIG. 5, an embodiment of a computer-implemented method 200 is shown for improving the function of a computer 124 for facilitating the diagnosis of a pathology of a non-carotid artery or other vasculature by analyzing, in some embodiments using machine learning, a spectral Doppler sonogram image of blood flow in the vasculature. The computer-implemented method 200 may be a corollary to the functionality of the above-described system 120, and may be similarly implemented using the various components of the system 120 within the above-described exemplary operating environment or other context. In addition, the steps of the method 200 may be, in whole or in part, performed by the system 120 executing the computer program stored on the memory elements 128 of the computer 124. Broadly, the method 200 may proceed substantially as follows. A sonogram image 134 of a non-carotid vasculature of a subject 132 may be generated by an ultrasound machine 122 and received by a processing element 126 of a computer 124, as shown in Step 222.

Next, the processing element 126 of the computer 124 may extract a set of quantitative waveform parameters from the sonogram image 134. In certain embodiments, extracting the set of waveform parameters may include finding a region of interest 136, generating a waveform envelope 137 for the waveform included within the region of interest 136, producing an extracted waveform 138 from the waveform envelope 137, performing a discrete Fourier transform on the extracted waveform 138, and generating a Fourier spectrum 140, wherein the Fourier spectrum comprises the set of waveform parameters. In addition, or in alternative to the Fourier spectrum 140 (e.g., temporal and/or spectral features of the waveform), the waveform parameters may include the peak value of the waveform (e.g., "P" from FIG. 1), the trough value of the waveform (e.g., "S" from FIG. 1), the acceleration and/or the time between the peak value and the trough value of the waveform (e.g., "t" from FIG. 1), the mean value of the waveform, the wavelength of the waveform, the frequency of the waveform, or other waveform data that can be measured and/or extracted from the waveform.

Figure 6:
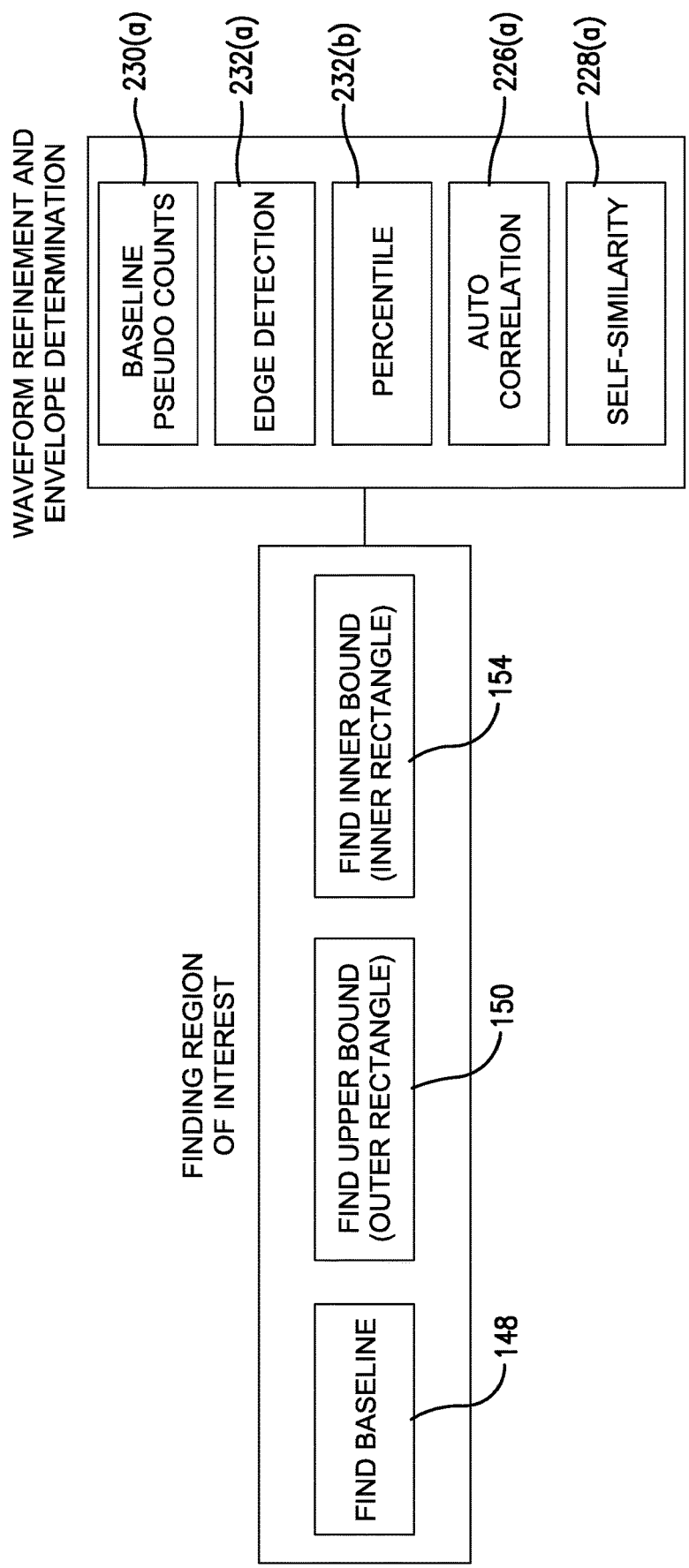
FIG. 6 is a flowchart of steps for generating a waveform envelope for a waveform from the sonogram image and for extracting a waveform, according to embodiments of the present invention.

In more detail, a region of interest 136 within the sonogram image 134 may be found by the processing element 126, as shown in Step 224. In one embodiment, referring also to FIGS. 3 and 6, instrumental parameters of the ultrasound machine 122 may be used to locate the baseline 148 and the upper bound 150 (defining an "outer rectangle") of the initial region of interest of the sonogram image 134. Thus, a first step in the analysis of the sonogram image 134 may be to identify a region of interest within the sonogram image 134, with such region of interest generally including at least a portion of the waveform. For example, as noted above, embodiments may generate the outer rectangle (defined by a baseline 148 and an upper bound 150) that encompasses the waveform. In some embodiments, such outer rectangle may be automatically generated by the inherent settings of the ultrasound machine 122 and/or the display device 130. In alternative embodiments, the outer rectangle may be formed using specific patterns of solid white pixels for determine the baseline 148 and solid black pixels for determining the upper bound 150. The baseline 148 of the sonogram image 136 may be found by the computer program by looking for a long horizontal pixel row of a given color (e.g., solid white), allowing some tolerance of short gaps due to baseline 148 wrapping. Using the machine preset area (e.g., including the upper bound 150) and the baseline 148, an outer rectangle can generally encompass the waveform accurately. In some instances, however, at least a portion of the waveform may be present below the baseline 148. In such instances, the waveform may be mirrored over the baseline 148, so that the region of interest will always be upright above the baseline to simplify extraction of the waveform parameters.

Depending on the blood flow velocity unit scaling and the waveform itself, a waveform may not fill up the entire outer rectangle region on the sonogram image 134, so refinement the region of interest vertically may be employed to reduce the region of interest to just the peaks of the waveform. For example, and with reference to FIGS. 3 and 6, the region of interest may be narrowed or reduced to a smaller rectangle (the "inner rectangle") defined at an upper side by an inner bound 154. In certain instances, this inner rectangle will more closely bound the waveform. The inner rectangle may be generated by analyzing the first and second derivatives, and the transition from bright to dark, of the marginal distribution of pixel brightness in the vertical dimension of the sonogram image 134. In other words, the waveform may be found below the region where the sharpest drop in average brightness occurs. As pixel rows of the waveform increase vertically, the sum of the brightness across the pixel rows will generally decrease. This is due to the pixel rows being made up of less of the waveform (i.e., shown as "white" pixels) and more of empty space or trough regions (i.e., shown as "black" pixels) as the rows are increased vertically. In some embodiments, a seventy-five percent difference in row brightness may be used as a threshold for identifying the tops of the peaks of waveform. Once the peaks of the waveform have been identified, the inner rectangle can be automatically generated so as to more closely encompass the waveform.

Embodiments of the present invention may also include horizontal refinements to the region of interest (e.g., when creating the outer or inner rectangle). Malformations and gaps in the waveform may pose issues when extracting the waveform and/or when obtaining waveform parameters. As such, certain embodiments of the present invention may reduce and/or reposition the horizontal extent of the region of interest so that the waveform included in the region of interest will not contain such malformations or gaps. Generally, embodiments of the present invention may require at least three waves of the waver in order to obtain accurate waveform parameters (e.g., so as to accurately calculate a SI for the waveform). As such, certain embodiments of the present invention are configured to establish the region of interest so as to include at least three contiguous waves within the waveform, with such waves being generally free from malformations and gaps. To accomplish such identification of preferential waves, embodiments of the present invention may include and utilize an autocorrelation methodology that identifies three contiguous waves within the waveform, with such waves sharing a highest similarity in size and shape.

Once the region of interest has been established, embodiments may further isolate corrupted section of the waveform by the processing element 126, as shown in Step 226 of the method 200 of FIG. 5. As will be described in more detail below, autocorrelation (See autocorrelation 226(*a*) of FIG. 6) may be used to find a putative frequency of the waveform, which may be followed by dividing the sonogram image 134 into slices, according to the putative frequency, with each slice corresponding to the estimated wavelength of the waveform. The slices (each associated with an individual wave) may be aligned with each other to identify waves (or parts of waves) of the waveform that are markedly dissimilar to the other waves. The corresponding subsequence of dissimilar waves in the sonogram image 134 may, in some embodiments, be eliminated from further analysis.

Furthermore, embodiments may provide for optimal sonogram waveform subsequences (i.e., sequences of waves within the waveform) to be determined by the processing element 126, as shown in Step 228. This refinement of the sonogram image 134 may involve finding the best sequence of three cycles of the signal (i.e., cycles without or at least with the fewest malformation and gaps) in a given sonogram. More specifically, as was noted above, calculating the SI for the waveform generally requires three waves of information. Thus, certain embodiments provide for the identification of at least three contiguous waves that have the highest self-similarity (See self-similarity 228(*a*) of FIG. 6), e.g., as perhaps defined by a self-similarity score. Focusing on the best three-wave subsequence of the sonogram waveform may increase the accuracy of the waveform parameters, so as to decrease the error associated with the determination of the likelihood of pathology. In one implementation, the optimal sonogram waveform subsequences may be found by shifting a copy of the waveform against itself for comparison, such that when the compared waveforms are in phase a minimum error is achieved and when the compared waveforms are out of phase a maximum error is achieved.

Figure 7:
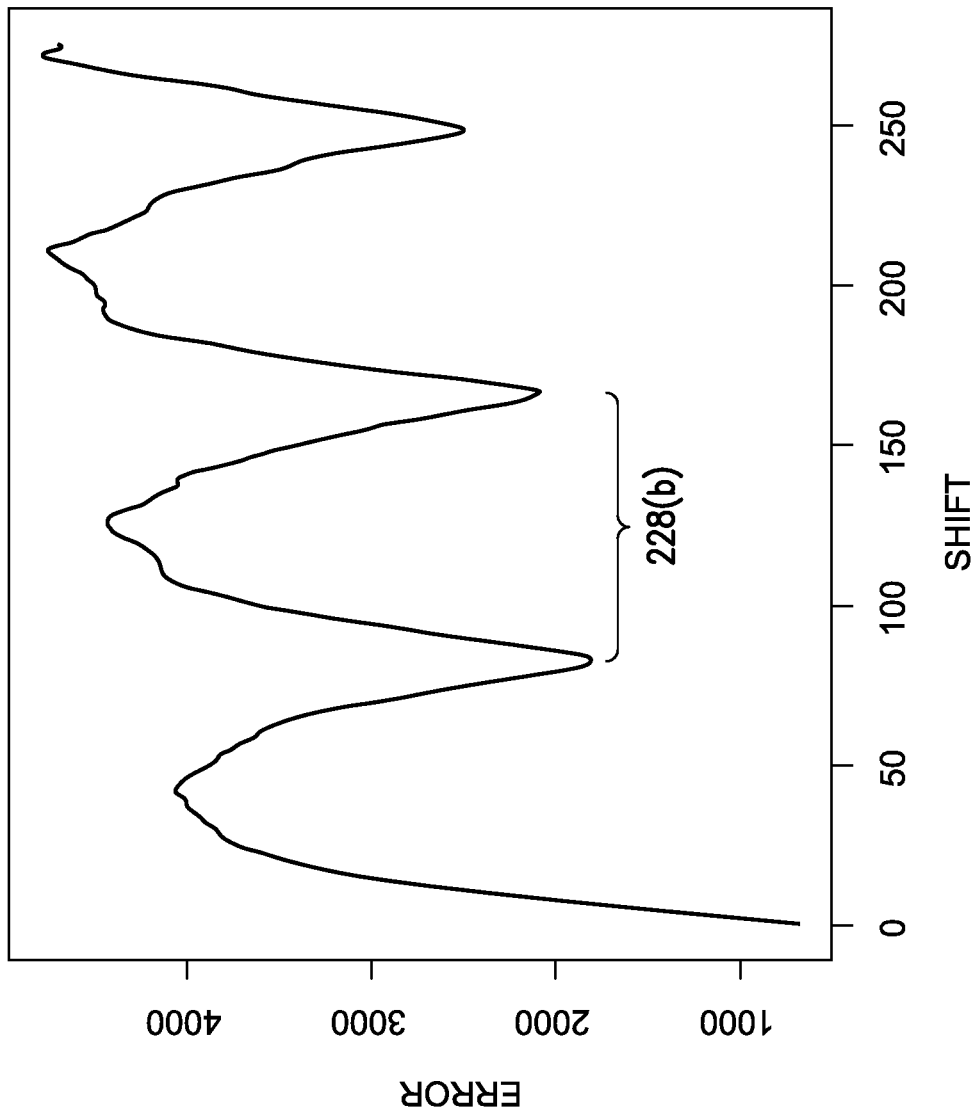
FIG. 7 is a graph of a waveform error, used according to embodiments of the present invention, to obtain a global waveform frequency.
Figure 8:
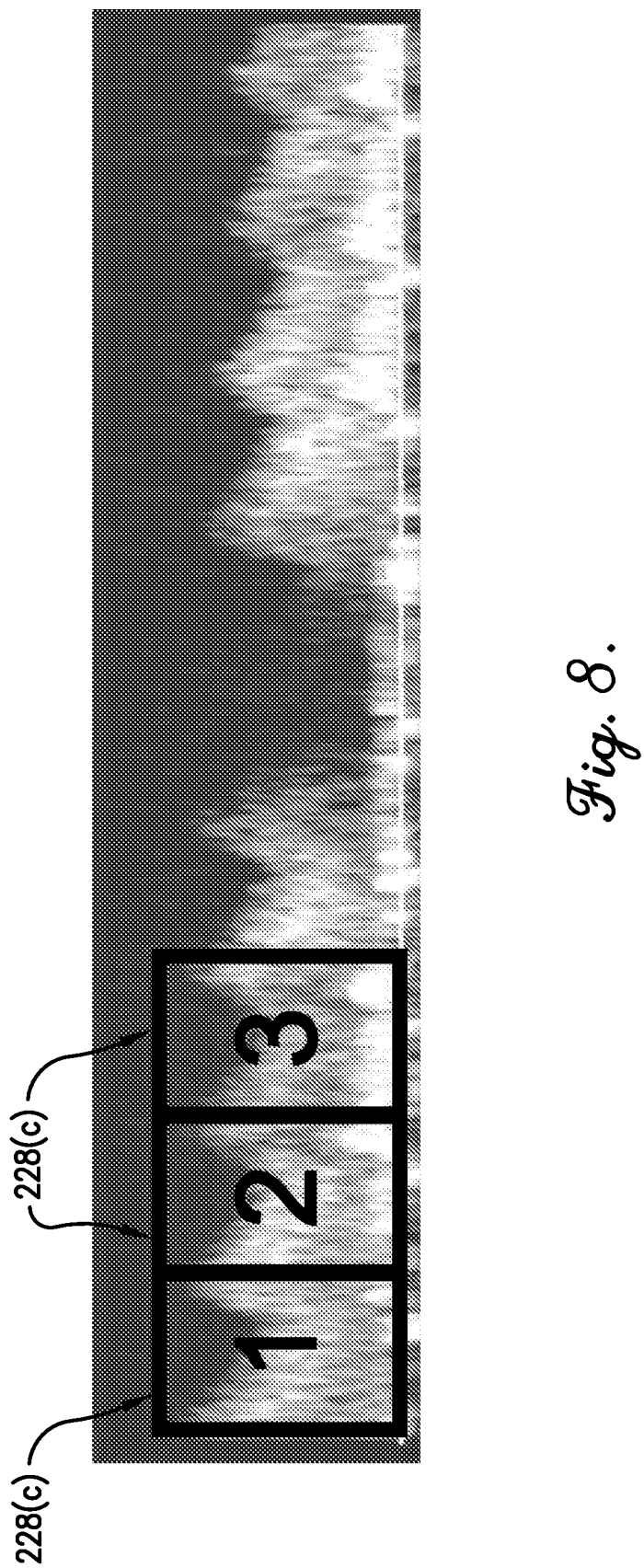
FIG. 8 is a graph of a waveform overlaid with three panels that divide the waveform into three slices according the global waveform frequency from FIG. 7.

In more detail, embodiments may generate a copy of the original waveform from the sonogram image 134. The copied waveform may be time-shifted and compared with the original waveform. When the compared waveforms are in phase, a minimum error is achieved, and when the compared waveforms are out of phase, a maximum error is achieved. A graphical plot of such errors can be generated, as illustrated in FIG. 7. A distance between subsequent minimum errors can be determined and used as an estimate of a global frequency 228(*b*) of the waveform. In some embodiments, the error may be normalized based on the number of points (e.g., pixels) in the waveforms that are compared with each other. The global frequency can then be used to generate a region of interest comprising three contiguous panels 228(*c*) that each extend over one wave from the waveform, as illustrated in FIG. 8. Such panels 228(*c*) can be used to divide the waveform into slices, as was discussed above. The similarity of the waves covered by the panels 228(*c*) (i.e., the wave of each slice of the waveform) may be computed using a sum of squares error methodology or using a modified metric. The panels 228(*c*) can then be shifted across the waveform, where the similarity at each shifting can also be computed.

Furthermore, the length of each panel 228(*c*) can be extended or reduced based on the size of the global frequency, and shifting and scoring can be performed again, normalized by the number of points used in the comparisons. The modification of the length of the panels 228(*c*) may be beneficial, as waves within certain waveforms can have slightly higher or lower frequency than the global frequency. Such variation may be due to either error in estimating the global frequency or wave variation. Thus, the modification of the panel 228(*c*) lengths may be used to find better fits for waves.

In further embodiments, an alternative refinement process for minimizing noise and malformations in the waveform may be used. In particular, using a wave apoptosis process, the global frequency found through autocorrelation methods described above can be used to divide the waveform into the waveform's individual waves. Thereafter, the similarity of each wave can be determined with respect to all other waves, resulting in a similarity matrix. The rows of the matrix can be summed to find the total error that a wave has with all other waves. The most-errored wave (with the highest summed error) and the least-errored wave (with the lowest number of errors) can be selected for further use. These waves can be used to cluster the remaining waves, so the waves with lower error and, thus, more similar to the least-errored wave will be clustered to the least-errored wave. Similarly, the waves with the highest error can be clustered with the most-errored wave. The waves similar to the most-errored wave can be removed and an average wave (or, alternatively, a median wave) can be generated from the remaining waves. The average wave can be replicated across the entire form. Different frequencies between waves within a waveform can affect the wave apoptosis process; if the peaks are slightly shifted away from each other while calculating the average wave, the average wave becomes malformed and rectangular. This outcome can also occur if the global frequency isn't correctly estimated. Peak shifting and single wave rescaling may be implemented to correct such problems.

In additional embodiments, a signal noise in the waveform of the sonogram image 134 may be compensated by the processing element 126, as shown in Step 230 of the method 200 of FIG. 5. In particular, instantaneous mean velocities within the region of interest (local mean at every time point) may be calculated first. The sonogram image 134 may then be padded with artificial pseudo counts (as described in more detail below) up to half of the mean instantaneous velocity. This may be done to compensate for random noise above the waveform, but without altering the outline of the waveform.

In more detail, the waveform from the sonogram imaged 134 may be further refined to improve the quality and accuracy of the waveform as a representation of the blood flow through the subject's 132 vasculature. To accomplish such refinements, pseudo counts may be added to the waveform to refine the waveform. Pseudo counts may be pixels that are activated from black to white so as to represent active portions of the waveform within the sonogram image 134. With some ultrasound machines 122, a horizontal row of black pixels will commonly be added above and/or below the baseline 148, as such a row of black pixels can helps to distinguish the baseline 148 from the waveform for the technologist operating the ultrasound machine 122. The additional row of black pixels can affect waveform characteristics, primarily the mean velocity value of the waveform. As such, embodiments of the present invention provide for pseudo counts, in the form of a horizontal row of baseline pseudo counts (See baseline pseudo counts 230(*a*) in FIG. 6) comprising a row of white pixels, added to the waveform. In some embodiments, such a row of baseline pseudo counts will be added to the waveform adjacent to the baseline 148. Such pseudo counts will therefore increase the instantaneous blood flow velocity at a given point in time, as a white pixel will be added to each column (with each column representing a specific point in time). Additionally, holes (i.e., invalid black pixels) within the waveform can be mitigated by filling such holes with pseudo counts, thereby reducing the effect of holes on the waveform and/or on the waveform parameters extracted from the waveform. The use of pseudo counts may also help with percentile extraction. By inflating the brightness distribution close to the baseline 148, the percentiles are shifted further towards the true waveform, away from noise, especially in sonogram images 134 where noise brightness is darker than the waveform.

Furthermore, embodiments of the present invention provide for additional waveform refinements to be used. For example, in some embodiments, one dimensional horizontal Gaussian blurring may be applied to the waveform, initially with a standard deviation of 3 pixels. The noise above the waveform on the sonogram image 134 is commonly skinny and tall. The use of horizontal blurring can reduce the intensity or brightness of such noise. Horizontal Gaussian blurring can also aid in filling in gaps across the top of the waveform. It should be understood, however, that blurring can alter a waveform envelope that is generated for the waveform, smearing the peaks, and changing the underlying frequency distribution. As such, the value of reducing noise and producing a truer extracted waveform must be weighed against affecting the resulting waveform envelope. Asymmetric Gaussian blurring may also be used to refine the waveform.

In certain specific embodiments, one-dimensional Gaussian blurring may be used to refine the image to negate random noise by averaging over several pixels as well as smoothen the waveform. To compute the blur of a given pixel, an interval of a set radius about it has Gaussian proportions assigned to each point and then averaged using those proportions. Mathematically, the weighting mechanism for a pixel can be defined as:

$$W(x) = \frac{1}{\sqrt{2\pi\sigma^2}} e^{\frac{-x^2}{2\sigma^2}}$$

for pixel x and standard deviation σ. However, it should be understood, that it may be undesirable for troughs and peaks of the waveform to be blurred with the same standard deviation. That is, when calculating the blur of a trough near the end of a wave, it may not be preferable to blur the rising peak to the right of the trough into the trough, as such a blurring may affect the true trough. Also, in some embodiments, it may be preferable to blur regions of high change and discontinuity differently than regions of low change and discontinuity. To allow for this, a hyperparameter may be utilized to account for the slope and continuity as well as the wave contextualization of peak and trough. In addition, some embodiments provide for two different standard deviations to be chosen for the baseline blurring effect for peak and trough separately. These values may be further augmented based on the slope and concavity at the pixel in question.

In addition to generating the region of interest, and refining the waveform included within the region of interest, embodiments may automatically extract additional information from the sonogram image 134. For example, the unit scaling for the blood flow velocity through the hepatic artery may be automatically obtained. Both the unit scaling for the blood flow velocity through the hepatic artery (i.e., the y-axis on the sonogram image 134 bounded by box 360), and the unit scaling for the time at which the blood flow is measured (i.e., the x-axis on the sonogram image 134 bounded by box 362) may be automatically obtained, such as via object character recognition (OCR). Such features may be rescaled by a scaling factor of the sonogram image 134. This scaling factor may, in some embodiments, also be obtained through OCR. When extracting the unit scaling, the sonogram image 134 may also be automatically cropped to only include the y-axis and x-axis of the waveform as to remove as much of the other visual data as possible. In some instances, OCR may misread dashes and numbers. Thus, in some embodiments, a regular expression may be created to exclude any non-numerical characters generated. The scaling factor can then be self-validated by iterating through the entire scale to validate the y-scaling chosen. That is, the difference between each successive pair of the y-axis generated from OCR can be found and the most consistent number can be used as the scaling factor. For the x-axis, only the number near the bottom of the screen may be read. Finally, the distances between tick marks in both the x and y directions can be used to produce the scaling factor. The features can then be converted into appropriate units and saved to a text file for further analysis or use.

Figure 9:
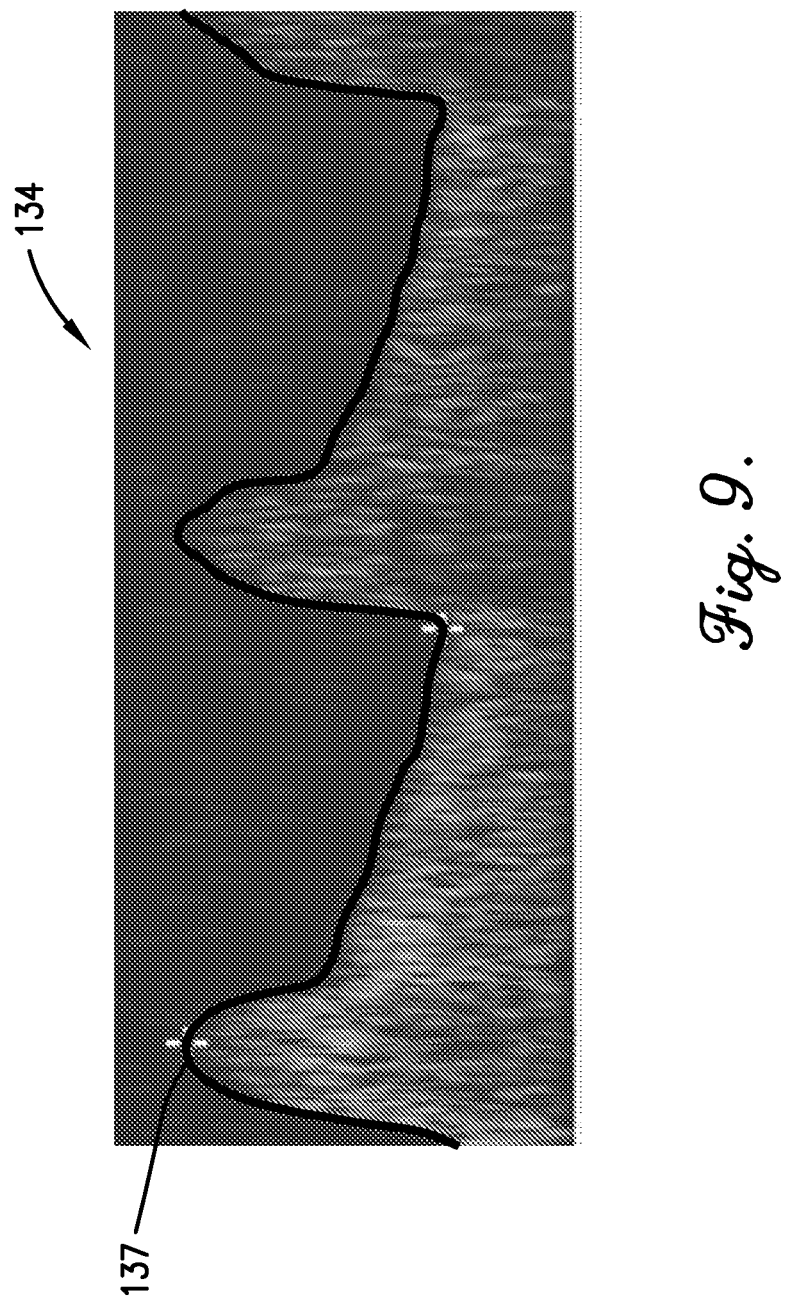
FIG. 9 is a graph of a waveform illustrating a waveform envelope generated for the waveform, according to embodiments of the present invention.

Returning to FIG. 5, the method 200 may additionally provide for the waveform envelope 137 (See FIG. 4) to be generated for the waveform via the processing element 126, as shown in Step 232. Broadly, the waveform envelope 137 may be a curve that forms an upper envelope for the waveform. As such, the waveform envelope 137 may comprise a smooth curve the represents the maximum velocity of the blood flow at each given point in time. Stated differently, the waveform envelope 137 represents a time-valued function of the blood-flow velocity represented by the sonogram image 134. For example, referring to FIG. 9 for more detail, the waveform envelope 137 is shown as the crest of the waveform representing the instantaneous peak velocity of the blood flow, which is highest during systole and lowest during diastole. In some embodiments, the waveform envelope 137 may alternatively be considered as a vertical refinement of the region of interest down to the top of the waveform.

In some embodiments, to generate the waveform envelope 137, a Prewitt filter may be used on the waveform to look for vertical edges under the condition that the waveform, generally being illustrated with white pixels, is positioned on the bottom of the sonogram image 134 and the black-pixeled background is positioned above the waveform. Alternatively, in some embodiments, a horizontal edge detection filter (See edge detection 232(a) from FIG. 6) may be used on the waveform to generate the waveform envelope 137. In one implementation, the filter may be an hourglass horizontal edge filter. The hourglass horizontal edge filter may be configured as a mask that integrates the differences in intensities of a local area above and below a given pixel, so that an edge of white waveform below and dark background above scores the highest. In more detail, for a given column, the edge score of each pixel can be calculated, where the pixel with the highest edge score is chosen. This methodology may be further enhanced by taking into account what percentile the pixel is at within the marginal distribution of the instantaneous blood flow velocity. That is, if a pixel is high, the edge probably may be due to noise, especially in the trough region, and if the pixel was too low, the pixel may likely be an inner edge.

Figure 10:
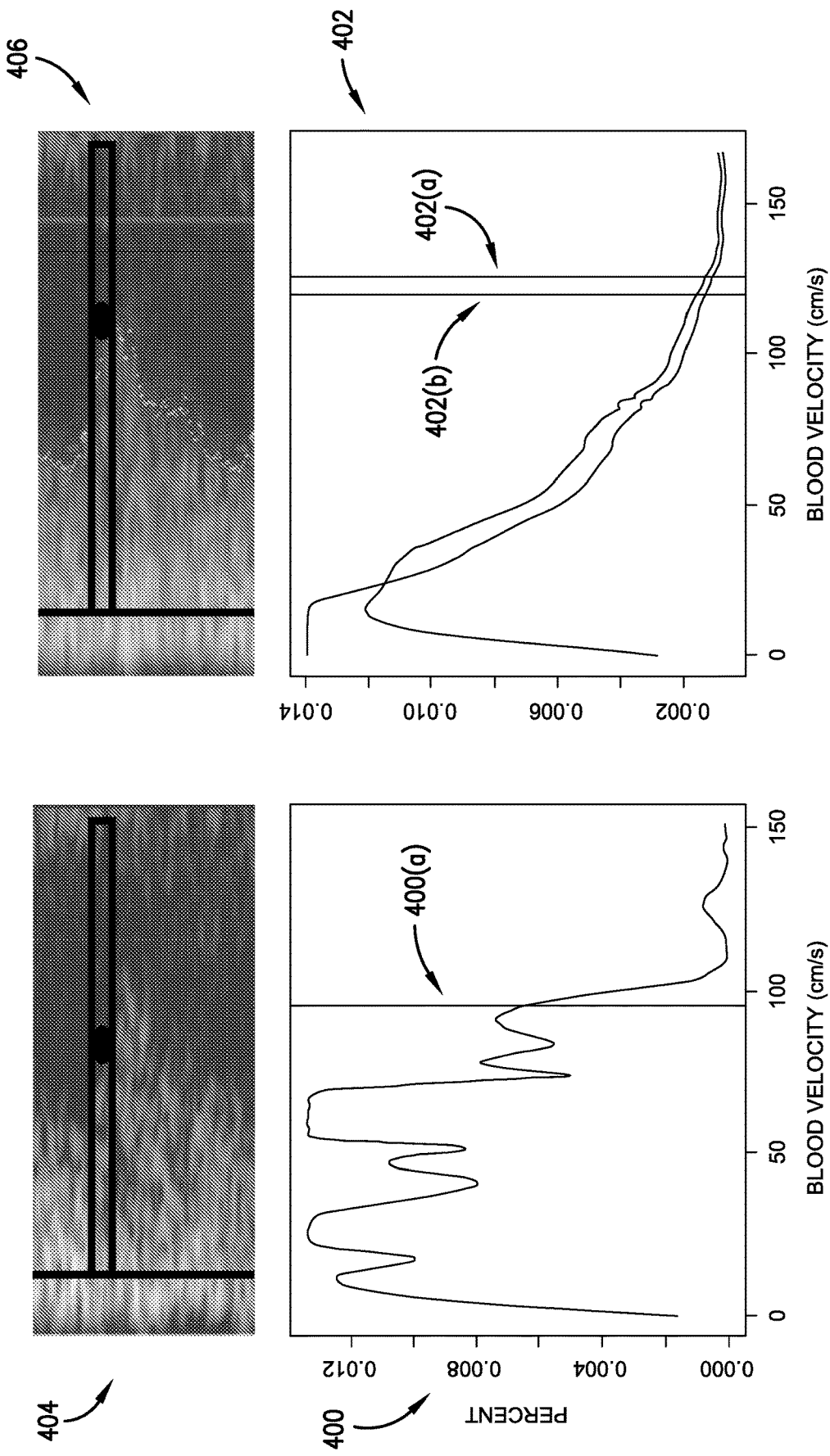
FIG. 10 is images of unaugmented and augmented sonograms and corresponding graphs of an instantaneous distribution of velocity corresponding to a single time point of the sonograms.

Additionally, or alternatively, the waveform envelope 137 may be generated for the waveform within the region of interest 134 by analyzing the distribution of velocity at each point in time to find the 95th percentile of the instantaneous velocity distribution. This may be taken to be the estimate of the local peak velocity or the top of the waveform at each time point. In FIG. 10, the graphs 400,402 of the lower panels show the instantaneous distribution of velocity corresponding to a single time point of the respective sonogram images 404,406 in the above panels and corresponding to the 95th percentile value of blood flow. Specifically, the vertical line 400(a) from graph 400 represents the 95th percentile value of blood flow velocity for the time point highlighted in sonogram image 404. The sonogram image 404 is unaugmented. In contrast, the sonogram image 406 on the right has been augmented with pseudo counts to skew the velocity distribution. As a result, the vertical line 402(a) illustrates the original 95th percentile value of blood flow, while the vertical lines 402(b) represents the augmented 95th percentile 95th percentile value of blood flow shifted to a lower velocity due to the use of the pseudo counts. Thus, the 95th percentile value may be recalculated after padding with pseudo counts.

In more detail, the 95th percentile of a given column (with the column representing one time point on the waveform) can be taken as the estimate for where the waveform envelope 137 resides in that column. The presence of pseudo counts can be used to reduce the impact noise has at shifting the estimation away from the waveform, especially in the trough region. The percentile methodology may be further extended to account for distance changes as percentile changes. On a perfect waveform, the waveform envelope 137 may be compressed as the percentile methodology may biasedly lower the peaks of the waveform more pixels than it would the troughs of the waveform. Since this is not a mere vertical shifting, the underlying frequency distribution can differ, affecting the resulting waveform data. As such, the percentile methodology may be further enhanced to compare pixel distances with oscillations to the percentile chosen for extraction. That is, if a change in a percentile, e.g., from 95th to 94th, changes the pixel distance greater than a threshold value, then the estimated point on the waveform envelope 137 has moved from a noise region closer to the waveform. If the estimated point on the waveform envelope 137 has moved less than that threshold value, it likely has moved further down within the waveform or further down a bright pocket of noise.

Similarly, if an estimated point on the waveform envelope 137 has moved from a smaller percentile, e.g., from 80th to 81st, and the point moves a distance greater than a threshold value, it is likely moving from the waveform to noise or across a hole inside the waveform. If the point moves less than the threshold value, it is likely moving up the waveform towards the top of the waveform and should continue. For this percentile methodology, a random upper and lower percentile may be chosen and moved lower and upper respectively until the pixel distance traveled is not high in the upper to lower case and is high in the lower to upper case (choosing the lower bound as the estimated point on the waveform envelope 137). If the values agree, the estimated point may be chosen as being part of the waveform envelope 137 (i.e., for that column). Points where the extracted values are not within the threshold may use neighboring points where the two estimations do agree to determine which estimation to use, choosing which estimation gives a value closer to its. Such use of neighboring points is defined herein as "Go Fish" extraction as the extraction "fishes" for a point from above and within the waveform.

Additionally, or alternatively, the waveform may also be contextualized, that is the regions that are peaks and troughs may be identified and labeled as such. Such contextualization allows re-refinement of Gaussian blurring, as specific zones can be targeted for different blurring intensities. Peaks may be located first by finding a region of points on the waveform envelope 137 that contain the highest average values without much spread between points. Troughs may then be found by looking between peaks for the lowest average value without much spread between points. Finally, these zones may be expanded by comparing neighbors of known peak or trough points and seeing to which they should belong.

Once the waveform envelope 137 has been generated for the waveform, method 200 additionally includes Step 234, which provides for the processing element 126 to extract the waveform envelope 137 to generate the extracted waveform 138, which is illustrated in FIG. 4. Thus, the extracted waveform 138 may comprise the waveform envelope 137 isolated from the remaining portion waveform. In some embodiments, the extracted waveform 138 may be separately plotted, as shown in FIG. 4. Next, a discrete Fourier transform may be performed on the extracted waveform envelope 138 and a Fourier spectrum 140 (e.g., the quantitative waveform parameters) may be generated by the processor 126, as shown in Step 236. Furthermore, embodiments provide for a pathology prediction value to be generated based on the extracted waveform 138, including from waveform parameters obtained from the extracted waveform 138 as shown in Step 238 of FIG. 5. In some embodiments, the waveform parameters will be the Fourier spectrum, and the pathology prediction value will be the SI. Alternatively, the waveform parameters may comprise other data obtained from the waveform, in which case the pathology prediction values may comprise other stenosis indicators (e.g., Resistive Index, Pulsatility Index, etc.). Nevertheless, the pathology prediction value may be generally any type of index or value that provides an estimate or indication of pathology for stenosis, and which, in some embodiments, is based on waveform parameters obtained from the extracted waveform 138.

Returning in more detail to SI, the SI can be calculated based on the Fourier analysis (e.g., from the Fourier spectrum 140). Specifically, the ratio of the high frequency components to low frequency components may be used to determine the presence of stenosis. For the other stenosis indicators (e.g., features 28 from FIG. 1, including the Resistive Index and Pulsatility Index) the ratio indices can be generated from other waveform parameters obtained from the waveform envelop 137 and/or the extracted waveform 138. Such waveform parameters may include the peak value of the waveform (e.g., "P" from FIG. 1), the trough value of the waveform (e.g., "S" from FIG. 1), the acceleration and/or the time between the peak value and the trough value of the waveform (e.g., "t" from FIG. 1), the mean value of the waveform, the wavelength of the waveform, the frequency of the waveform, or other waveform data that can be measured and/or extracted from the waveform. The cancellation of pixel scaling aids in the calculation and use of such ratio indices. Thus, in some embodiments, the pathology prediction value may be calculated based on a power distribution of the Fourier spectrum 140 by taking a ratio of the power in the high frequency components to that in the low frequency components of the Fourier spectrum 140. Additional indicators, such as an RI, acceleration time, global frequency, and/or right and left half-lives, may also be generated from the waveform parameters obtained from the extracted waveform 138, as necessary, for purposes of generating a pathology prediction value.

Some alternative embodiments provide for the pathology prediction value to be determined from the set of quantitative waveform data by the processor 126 using a machine learning component of the computer program (i.e., stored on the memory elements 128), as executed by the processing element 126. The machine learning component may use machine learning models to classify and diagnosis stenosis of the subject 132, which may, in some embodiments, include generating a pathology prediction value based on waveform parameters obtained from the extracted waveform 128. For example, Naïve Bayes, decision trees, and random forests may be used as machine learning models. Naïve Bayes estimates the probability of stenosis under the assumption of conditional independence of features and may be utilized, in some embodiments, as a baseline to determine how much predictive power may be gained from machine learning models. Decision trees may be used to partition the training space to either minimize misclassification, with the Gini impurity metric, or gain the most information, based on entropy. For example, the waveform parameters obtained from the extracted waveform 138 may be compared with one or more decision tree models to determine a pathology prediction value and/or a likelihood of pathology. Decision trees benefit from high interpretability but are not guaranteed to generate an optimal model. Random forests are a modified ensemble of decision trees, each with its own data set generated by random subset of the feature set. The use of sampled features, and no pruning, can generate a decision tree which, when taken individually is a high variance model. Random forests tend to overfit less to the training set as they are an average of these high variance unpruned trees; however, as more trees are utilized, the interpretability of the model decreases. Cross validation may be utilized with all models at 10-fold cross validation to decide the best model for implementation.

In more detail, certain embodiments of the machine learning component may use a random forest model, in which a number of decision trees are used to generate a final output which is a combination of the trees. Each decision tree can include one or more internal nodes connected to leaf nodes via branches comprising decision rules. For example, such decision rules may comprise if/else or if/then rules. The decision rules may be used to analyze one or more of the waveform parameters to determine which branches are the correct branches to be traversed. By applying the waveform parameters to the decision trees, embodiments can arrive at the appropriate outcome (e.g., the leaf nodes) for the extracted waveform 138 from which the waveform parameters were obtained. Such an outcome may be a likelihood of pathology and/or a pathology prediction value (also referred to as a pathology prediction). In some specific embodiments, the outcome may be a likelihood of pathology that is comprised of a pathology prediction value.

A random forest is a modified ensemble of decision trees. The use of sampled features, and without pruning, can construct a tree that, taken individually, is a high variance model. Random forests tend to overfit less to the training set as they are an average of these high variance unpruned trees. However, as more trees are utilized, the interpretability of the model decreases. An example random forest model, which may form part of the machine learning component of embodiments of the present invention, is provided at the end of this Detailed Description. The exemplary random forest model contains five decision trees, in which each if/else group represents a decision rule that can be used to analyze the waveform parameters obtained from the extracted waveform 138. In some embodiments, the number of decision trees can be set to 1000 trees, with a depth of 30 for random forests.

Thus, embodiments of the present invention include the use of decision trees to classify and diagnose pathologies, such as stenosis, by comparing the waveform parameters obtained from a waveform with decision trees that include values and decision rules for classifying and diagnosing stenosis. As more decision trees are used (particularly in a random forest model), the classification and diagnosis of pathologies, such as stenosis, can be significantly increased. For example, in some embodiments, a plurality of decision trees can be created from waveforms extracted from sonogram images of patients with and without stenosis. Thus, such decision trees can be classified (e.g., positive or negative for stenosis) and used for comparison with the waveform parameters to obtain a pathology prediction value (i.e., likelihood pathology). As more decision trees are obtained (e.g., for additional arterial sonogram images, sonogram images from left hepatic and right hepatic arteries), the use of such decision trees, particularly using a random forest modelling, can augment and enhance the ability for embodiments to generate accurate pathology prediction value for determining the likelihood of pathology.

In one embodiment, additional patient information about the subject 132 which is relevant to the pathology may be accessed by the processing element 126, as shown in Step 240 of method 200 of FIG. 5. Such additional patient information may be stored, for instance, on the memory element 128, and may include, for example, a level of liver or other enzymes in the bloodstream. The likelihood of the pathology may be determined by the processing element 126, e.g., using the machine learning component and/or otherwise based on the pathology prediction value, and, if used, the additional patient information, as shown in Step 240. In one implementation, the determined likelihood of the pathology may simply comprise the pathology prediction value.

An associated error value may be estimated by the processing element 126 for the determined likelihood of the pathology, as shown in 244. In one embodiment, a set of waveform envelopes 137 may be created by generating a waveform envelop 137 for a set of randomly chosen sonograms images 134. Some embodiments may include the generation of at least fifty randomly-generated waveform envelopes 137. Such randomly-generated waveform envelopes 137 may be compared with each method for predicting the accuracy and/or an error of the extracted waveform envelope 138 generated and extracted in the embodiments discussed above. Error may be estimated as the mean squared error and percent absolute error. The bias component of error may be estimated by calculating the mean difference between the prediction and the ground truth.

The determined likelihood of the pathology and the associated error value may be displayed on an electronic display 130 for consideration by a healthcare practitioner in the diagnosis of the pathology of the non-carotid vasculature, as shown in 246. In some embodiments, the likelihood of the pathology may be the pathology prediction value.

Although the above description primarily references the analysis of a spectral Doppler sonogram image to determine a likelihood of pathology and/or a pathology prediction value for stenosis, it should be understood that certain embodiments may analyze other types of data obtained from the ultrasound machine 122. For example, in certain embodiments raw data obtained from the ultrasound machine 122 may be analyzed to determine a likelihood of pathology and/or a pathology prediction value for stenosis. As the ultrasound machine 122 measures the velocity of blood flow (or other fluid flow) through the vasculature of the subject 132, the ultrasound machine 122 will generate raw data indicative of such blood flow velocity. Commonly, the raw data may be provided to an electronic display, whereby the electronic display converts the raw data into the spectral Doppler sonogram image 134 that is presented graphically on the electronic display. Nevertheless, certain embodiments of the present invention may include analyzing such raw data to determine a likelihood of pathology and/or a pathology prediction value for stenosis.

Broadly, such raw data may comprise a data stream representative of a measured blood-flow velocity of a subject 132 with respect to time. For example, as described above, graphs 400,402 from FIG. 10 show the instantaneous distribution of blood flow velocity corresponding to a single time point. Thus, the raw data may be interpreted as a histogram of blood flow velocity distributions (e.g., in a digital or analog format) for each time point that is measured. Embodiments of the present invention may be configured to analyze such raw data to determine a likelihood of pathology and/or a pathology prediction value for stenosis.

Figure 11:
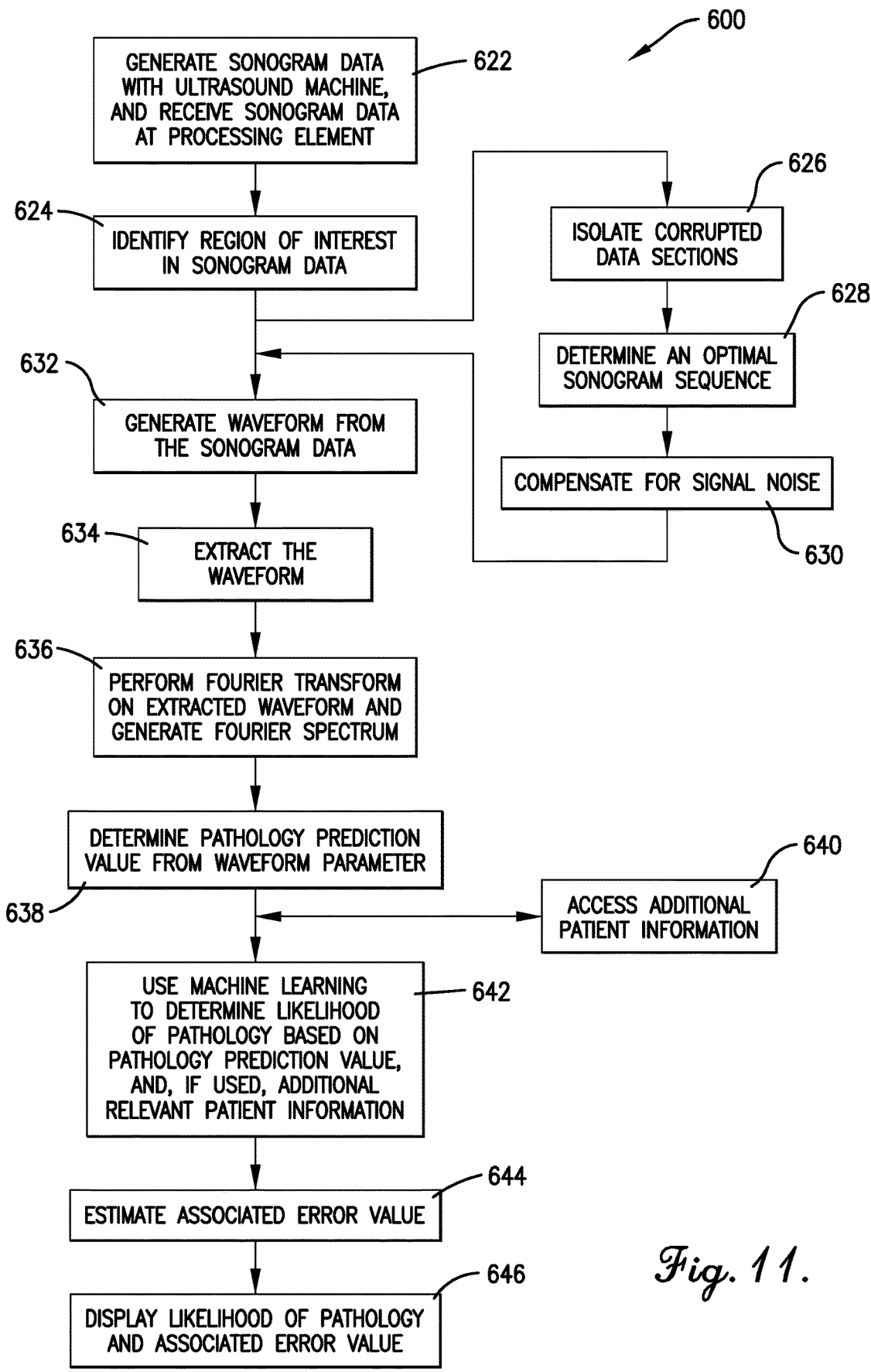
FIG. 11 is a flowchart of steps of another method for facilitating the diagnosis of a pathology of a non-carotid artery or other vasculature, according to embodiments of the present invention.

For example, with reference to FIG. 11, an embodiment of a computer-implemented method 600 is shown for improving the function of a computer 124 for facilitating the diagnosis of a pathology of a non-carotid artery or other vasculature by analyzing, in some embodiments using machine learning, spectral Doppler sonogram data of blood flow in the vasculature. The computer-implemented method 600 may be similarly implemented using the various components of the system 120 within the above-described exemplary operating environment or other context. In addition, the steps of the method 600 may be, in whole or in part, performed by the system 120 executing the computer program stored on the memory elements 128 of the computer 124.

Broadly, the method 600 may proceed substantially as follows. Sonogram data of a non-carotid vasculature of a subject 132 may be generated by an ultrasound machine 122 and received by a processing element 126 of a computer 124, as shown in Step 622. In some embodiments, the sonogram data may comprise raw data (e.g., in a digital or analog format) indicative of the instantaneous distribution of blood flow velocity for each point in time over a period of time. In Step 624, the processor may identify a region of interest within the sonogram data. Such identification of the region of interest may include: isolating corrupted data sections within the sonogram data, as shown in Step 626; determining an optical sonogram sequence of the sonogram data, as shown in Step 628; and compensating for signal noise in the sonogram data, as shown in Step 630.

Next, the method 600 may include generating a waveform from the sonogram image, as shown in Step 632, and extracting the waveform, as shown in Step 634. A Fourier transform may be performed on the extracted waveform so as to generate a Fourier spectrum, as shown in Step 636. In some embodiments, a pathology prediction value may be obtained from a waveform parameter of the extracted waveform, as shown in Step 638. In some embodiments, the waveform parameter may be the Fourier spectrum.

In some additional embodiments, additional patient information may be accessed, as shown in Step 640. As shown in Step 642, machine learning may be used to determine a likelihood of pathology based on the pathology prediction value and, if used, the additional patient information. In some embodiments, as shown in Step 644, an error value may be estimated for the likelihood of pathology. Thus, as shown in Step 646, the likelihood of pathology and the associated error value may be presented or displayed.

The computer-implemented methods 200 and 600 may include more, fewer, or alternative actions, including those discussed elsewhere herein. For example, in some embodiments, certain steps of the methods 200 and 600 described above may be optional or may be omitted. Additionally, the steps may be performed in different orders than described and shown.

Any actions, functions, steps, and the like recited herein may be performed in the order shown in the figures and/or described above, or may be performed in a different order. Furthermore, some steps may be performed concurrently as opposed to sequentially. Although the computer-implemented method is described above, for the purpose of illustration, as being executed by an exemplary system and/or exemplary physical elements, it will be understood that the performance of any one or more of such actions may be differently distributed without departing from the spirit of the present invention.

Certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as computer hardware that operates to perform certain operations as described herein.

A computer-readable medium comprising a non-transitory medium may include an executable computer program stored thereon and for instructing one or more processors to perform some or all of the actions described herein, including some or all of the steps of the computer-implemented method. The computer program stored on the computer-readable medium may instruct the processing element and/or other components of the system to perform additional, fewer, or alternative actions, including those discussed elsewhere herein.

The terms "processing element," "processor," and the like, as used herein, may, unless otherwise stated, broadly refer to any programmable system including systems using central processing units, microprocessors, microcontrollers, reduced instruction set circuits (RISC), application specific integrated circuits (ASIC), logic circuits, and any other circuit or processor capable of executing the functions described herein. The above examples are example only, and are thus not intended to limit in any way the definition and/or meaning of the terms "processing element" and "processor." In particular, "a processing element" and "a processor" may include one or more processing elements individually or collectively performing the described functions.

Accordingly, the term "processing element" or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a particular hardware configuration at one instance of time and to constitute a different hardware configuration at a different instance of time.

In addition, the terms "software," "computer program," and the like, may, unless otherwise stated, broadly refer to any executable code stored in memory for execution on mobile devices, clusters, personal computers, workstations, clients, servers, and a processor or wherein the memory includes read-only memory (ROM), electronic programmable read-only memory (EPROM), random access memory (RAM), erasable electronic programmable read-only memory (EEPROM), and non-volatile RAM (NVRAM) memory. The above memory types are exemplary only, and are thus not limiting as to the types of memory usable for storage of a computer program.

The terms "computer," "computing device," and the like, as used herein, may, unless otherwise stated, broadly refer to substantially any suitable technology for processing information, including executing software, and may not be limited to integrated circuits referred to in the art as a computer, but may broadly refer to a microcontroller, a microcomputer, a programmable logic controller (PLC), an application specific integrated circuit, and other programmable circuits, and these terms are used interchangeably herein.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Additional advantages of the various embodiments of the invention will be apparent to those skilled in the art upon review of the disclosure herein. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, and/or display information. As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

Although the invention has been described with reference to the embodiments illustrated in the attached drawing figures, it is noted that equivalents may be employed and substitutions made herein without departing from the scope of the invention as recited in the claims. Having thus described one or more embodiments of the invention, what is claimed as new and desired to be protected by Letters Patent provided below in the listing of claims.

Random Forrest Algorithm:
Tree 0:
If (feature 1<=0.5274725274725275)
  If (feature 0<=2.3817658387250664)
    Predict: 1.0
  Else (feature 0>2.3817658387250664)
    Predict: 0.0
  Else (feature 1>0.5274725274725275)
    If (feature 9<=0.19895161619773297)
      If (feature 12<=-0.15203211498311367)
        If (feature 0<=1.004143592962803)
          Predict: 1.0
        Else (feature 0>1.004143592962803)
          Predict: 0.0
      Else (feature 12>-0.15203211498311367)
        Predict: 0.0
    Else (feature 9>0.19895161619773297)
      If (feature 14<=-0.00491148232899101)
        Predict: 0.0
      Else (feature 14>-0.00491148232899101)
Predict: 1.0
Tree 1:
If (feature 9<=0.055333786168262795)
  If (feature 9<=-0.2894794937905121)
    If (feature 13<=-0.29854339172120126)
      Predict: 0.0
    Else (feature 13>-0.29854339172120126)
      Predict: 1.0
  Else (feature 9>-0.2894794937905121)
    If (feature 14<=-0.07567837736648172)
      Predict: 1.0
    Else (feature 14>-0.07567837736648172)

```
        If (feature 13<=0.06781632009533631)
            Predict: 0.0
        Else (feature 13>0.06781632009533631)
            Predict: 0.0
    Else (feature 9>0.055333786168262795)
        If (feature 15<=-0.0050153389617698276)
            Predict: 1.0
        Else (feature 15>-0.0050153389617698276)
            If (feature 10<=-0.25732600301795433)
                Predict: 1.0
            Else (feature 10>-0.25732600301795433)
                If (feature 10<=0.1339362686430594)
                    Predict: 0.0
                Else (feature 10>0.1339362686430594)
                    Predict: 1.0
Tree 2:
If (feature 0<=1.471087111030766)
    If (feature 9<=0.055333786168262795)
        If (feature 14<=-0.075678377366648172)
            Predict: 1.0
        Else (feature 14>-0.075678377366648172)
            If (feature 11<=-0.3196902184709339)
                Predict: 1.0
            Else (feature 11>-0.3196902184709339)
                Predict: 0.0
    Else (feature 9>0.055333786168262795)
        Predict: 1.0
Else (feature 0>1.471087111030766)
    If (feature 15<=0.1852411133200483)
        If (feature 0<=1.616023424825236)
            If (feature 10<=-0.14158292160095193)
                Predict: 0.0
            Else (feature 10>-0.14158292160095193)
                Predict: 1.0
        Else (feature 0>1.616023424825236)
            Predict: 0.0
    Else (feature 15>0.1852411133200483)
        Predict: 1.0
Tree 3:
If (feature 0<=0.9836346303581093)
Predict: 1.0
Else (feature 0>0.9836346303581093)
    If (feature 13<=-0.06745138869697512)
        If (feature 1<=0.48135593220338985)
            Predict: 1.0
        Else (feature 1>0.48135593220338985)
            If (feature 1<=0.7763157894736842)
                Predict: 0.0
            Else (feature 1>0.7763157894736842)
                Predict: 1.0
    Else (feature 13>-0.06745138869697512)
        If (feature 12<=-0.263366230414587)
            If (feature 5<=0.051470588235294115)
                Predict: 0.0
            Else (feature 5>0.051470588235294115)
                Predict: 1.0
        Else (feature 12>-0.263366230414587)
            If (feature 4<=2.1176470588235294)
                Predict: 0.0
            Else (feature 4>2.1176470588235294)
                Predict: 1.0
Tree 4:
If (feature 1<=0.5050505050505051)
    If (feature 5<=0.21323529411764705)
        Predict: 1.0
    Else (feature 5>0.21323529411764705)
        Predict: 0.0
Else (feature 1>0.5050505050505051)
    If (feature 4<=2.1176470588235294)
        If (feature 2<=0.6838235294117647)
            Predict: 1.0
        Else (feature 2>0.6838235294117647)
            If (feature 15<=0.1852411133200483)
                Predict: 0.0
            Else (feature 15>0.1852411133200483)
                Predict: 1.0
    Else (feature 4>2.1176470588235294)
    Predict: 1.0
```

The invention claimed is:

1. A system for facilitating an evaluation of non-carotid vasculature and blood flow through said non-carotid vasculature of a subject, the system comprising:
   an ultrasound machine configured to generate spectral Doppler sonogram data of blood flow velocity for the non-carotid vasculature;
   a processing element configured to extract a set of waveform parameters from the spectral Doppler sonogram data of blood flow velocity, said processing element further configured to perform a machine learning process including—
   generating a plurality of decision trees,
   evaluating the spectral Doppler sonogram data of blood flow velocity and extracted waveform parameters using the plurality of decision trees, and
   generating a pathology prediction value; and
   an electronic display configured to display a likelihood of a pathology based on the pathology prediction value.

2. The system of claim 1, wherein the pathology is a stenosis pathology.

3. The system of claim 1, wherein the processing element is included in a computing device distinct from the ultrasound machine.

4. The system of claim 1, wherein the machine learning component uses a random forest model comprising a plurality of decision trees.

5. The system of claim 1, wherein the spectral Doppler sonogram data of blood flow velocity comprises a spectral Doppler sonogram image.

6. The system of claim 5, wherein the processing element is further configured to extract said set of waveform parameters from the spectral Doppler sonogram image, wherein the set of waveform parameters are extracted by—
   finding a region of interest in the spectral Doppler sonogram image,
   extracting a waveform from the region of interest to produce an extracted waveform, and
   performing a Fourier transform of the extracted waveform and generating a Fourier spectrum, wherein the Fourier spectrum is the set of waveform parameters.

7. The system of claim 6, wherein the waveform is extracted using an edge detection filter.

8. The system of claim 6, the processing element being further configured to, between extracting the waveform and performing the Fourier transform, compensate for signal noise in the extracted waveform, isolate a corrupted section of the extracted waveform, and determine an optimal waveform subsequence.

9. The system of claim 1, wherein the processing element is configured to access patient information about the subject, wherein the step of displaying the likelihood of the pathology is based on the pathology prediction value and the patient information.

10. A computer-implemented method for facilitating an evaluation of non-carotid vasculature and blood flow through said non-carotid vasculature of a subject, the computer-implemented method comprising:

generating using an ultrasound machine spectral Doppler sonogram data of blood flow velocity for the non-carotid vasculature;

extracting by a processing element a set of waveform parameters from the spectral Doppler sonogram data of blood flow velocity;

performing by a processing element a machine learning process including—
generating a plurality of decision trees,
evaluating the spectral Doppler sonogram data of blood flow velocity and set of waveform parameters using the plurality of decision trees, and
generating a pathology prediction value; and displaying on an electronic display a pathology prediction based on the pathology prediction value.

11. The computer-implemented method of claim 10, wherein the spectral Doppler sonogram data of blood flow velocity comprises a spectral Doppler sonogram image, wherein the conduit is a hepatic artery, and the pathology is a stenosis pathology, and wherein the computer-implemented method further includes the step of:

estimating by the processor an associated error value for the determined pathology prediction,
displaying on the electronic display the associated error value.

12. A computer-implemented method for improving the function of a computer for facilitating a diagnosis of a pathology of a non-carotid vasculature of a subject and blood flow through said non-carotid vasculature, the computer including a processor, the computer-implemented method comprising:

generating using an ultrasound machine and receiving by the processor spectral Doppler sonogram data of blood flow velocity for the non-carotid vasculature of the subject;

extracting by the processor a set of waveform parameters from the spectral Doppler sonogram data of blood flow velocity;

determining by the processor using a machine learning component a pathology prediction value from the set of waveform parameters;

determining by the processor using the machine learning component a determined likelihood of the pathology based on the pathology prediction value; and displaying on an electronic display the determined likelihood of the pathology for consideration by a healthcare practitioner in the diagnosis of the pathology of the non-carotid vasculature of the subject.

13. The computer-implemented method of claim 12, wherein the non-carotid vasculature is a hepatic artery, and the pathology is stenosis.

14. The computer-implemented method of claim 12, wherein the computer is incorporated into the ultrasound machine.

15. The computer-implemented method of claim 12, wherein the computer is distinct from the ultrasound machine.

16. The computer-implemented method of claim 12, wherein the machine learning component uses a random forest model comprising a plurality of decision trees.

17. The computer-implemented method of claim 12, wherein the spectral Doppler sonogram data of blood flow velocity comprises a spectral Doppler sonogram image, wherein extracting the set of waveform parameters from the spectral Doppler sonogram data of blood flow velocity includes—
finding a region of interest in the spectral Doppler sonogram image,
extracting a waveform from the region of interest to produce an extracted waveform, and
performing a Fourier transform of the extracted waveform and generating a Fourier spectrum, wherein the Fourier spectrum is the set of waveform parameters.

18. The computer-implemented method of claim 17, wherein the waveform is extracted using an edge detection filter.

19. The computer-implemented method of claim 17, further including, between extracting the waveform and performing the Fourier transform, compensating by the processor for signal noise in the extracted waveform, isolating by the processor a corrupted section of the extracted waveform, and determining by the processor an optimal waveform subsequence.

20. The computer-implemented method of claim 12, further including accessing by the processor additional patient information about the subject which is relevant to the pathology, wherein the step of determining the likelihood of the pathology is based on the pathology prediction value and the additional patient information.

* * * * *